US009951042B2

(12) United States Patent
Hilfiker et al.

(10) Patent No.: US 9,951,042 B2
(45) Date of Patent: Apr. 24, 2018

(54) POLYMORPHIC FORM OF [5-FLUORO-3-({2-[(4-FLUOROBENZENE) SULFONYL] PYRIDIN-3-YL}METHYL)-2-METHYLINDOL-1-YL]-ACETIC ACID

(71) Applicant: Atopix Therapeutics Limited, London (GB)

(72) Inventors: Rolf Hilfiker, Kaiseraugst (CH); Katja Grosse-Sender, Kaiseraugst (CH)

(73) Assignee: ATOPIX THERAPEUTICS LIMITED, London (GB)

( * ) Notice: Subject to any disclaimer, the term of this patent is extended or adjusted under 35 U.S.C. 154(b) by 0 days.

(21) Appl. No.: 15/308,290

(22) PCT Filed: May 1, 2015

(86) PCT No.: PCT/GB2015/051296
§ 371 (c)(1),
(2) Date: Nov. 1, 2016

(87) PCT Pub. No.: WO2015/166280
PCT Pub. Date: Nov. 5, 2015

(65) Prior Publication Data
US 2017/0121306 A1    May 4, 2017

(30) Foreign Application Priority Data

May 2, 2014 (GB) .................. 1407820.8

(51) Int. Cl.
*C07D 401/06* (2006.01)
*A61K 31/4439* (2006.01)
*A61K 31/47* (2006.01)

(52) U.S. Cl.
CPC ........ *C07D 401/06* (2013.01); *A61K 31/4439* (2013.01); *A61K 31/47* (2013.01); *C07B 2200/13* (2013.01)

(58) Field of Classification Search
CPC ... C07D 401/06; A61K 31/4439; A61K 31/47
See application file for complete search history.

(56) References Cited

U.S. PATENT DOCUMENTS

| | | |
|---|---|---|
| 3,557,142 A | 1/1971 | Bell |
| 3,843,683 A | 10/1974 | Bell |
| 4,273,782 A | 6/1981 | Cross et al. |
| 4,363,912 A | 12/1982 | Cross et al. |
| 4,478,842 A | 10/1984 | Renfroe |
| 4,774,240 A | 9/1988 | Böshagen et al. |
| 4,859,692 A | 8/1989 | Bernstein et al. |
| 5,214,059 A | 5/1993 | Tegeler et al. |
| 5,410,061 A | 4/1995 | Gilmore et al. |
| 5,496,844 A | 3/1996 | Inai et al. |
| 5,532,237 A | 7/1996 | Gallant et al. |
| 5,578,634 A | 11/1996 | Bach et al. |
| 5,641,800 A | 6/1997 | Bach et al. |
| 5,744,488 A | 4/1998 | Cross et al. |
| 6,500,853 B1 | 12/2002 | Seehra et al. |
| 6,521,659 B2 | 2/2003 | Sredy et al. |
| 6,555,568 B1 | 4/2003 | Sredy et al. |
| 6,602,890 B2 | 8/2003 | Höfgen et al. |
| 6,730,794 B2 | 5/2004 | Jones et al. |
| 6,797,708 B2 | 9/2004 | McKew et al. |
| 6,828,344 B1 | 12/2004 | Seehra et al. |
| 6,916,841 B2 | 7/2005 | Seehra et al. |
| 6,995,263 B2 | 2/2006 | Ackermann et al. |
| 7,166,607 B2 | 1/2007 | Bonnert et al. |
| 7,321,001 B2 | 1/2008 | Fu et al. |
| 7,348,351 B2 | 3/2008 | Jennings et al. |
| 7,405,215 B2 | 7/2008 | Bennani et al. |
| 7,534,897 B2 | 5/2009 | Tanimoto et al. |
| 7,582,672 B2 | 9/2009 | Middlemiss et al. |
| 7,601,749 B2 | 10/2009 | Bennani et al. |
| 7,750,027 B2 | 7/2010 | Armer et al. |
| 7,919,512 B2 | 4/2011 | Armer et al. |
| 7,999,119 B2 | 8/2011 | Armer et al. |
| 8,044,088 B2 | 10/2011 | Armer et al. |
| 8,163,931 B2 | 4/2012 | Middlemiss et al. |
| 8,163,936 B2 | 4/2012 | Middlemiss et al. |
| 8,168,673 B2 | 5/2012 | Armer et al. |
| 8,198,314 B2 | 6/2012 | Middlemiss et al. |
| 8,268,878 B2 | 9/2012 | Armer et al. |
| 8,314,257 B2 | 11/2012 | Middlemiss et al. |
| 8,536,158 B2 | 9/2013 | Armer et al. |
| 8,563,536 B2 | 10/2013 | Armer et al. |

(Continued)

FOREIGN PATENT DOCUMENTS

EP    0 054 417 A1    6/1982
EP    0 851 030 A1    7/1998
(Continued)

OTHER PUBLICATIONS

Medical Daily (2010).*
National Heart, Lung and Blood Institute How can Asthma be prevented(2014).*
Morissette et al. (Advanced Drug Delivery Reviews, 2004, vol. 56, pp. 275-300).*
Armer, R.E., et al., "Indol-3-acetic Acid Antagonists of the Prostaglandin $D_2$ Receptor CRTH2," *J. Med. Chem.* 48:6174-6177, American Chemical Society, United States (2005).
Caira, M.R., "Crystalline Polymorphism of Organic Compounds," *Topics in Current Chemistry* 198:164-208, Spinger Verlag Berlin Heidelberg, Germany (1998).
Cross, P.E., et al., "Selective Thromboxane Synthetase Inhibitors. 2. 3-(1H-Imidazol-1-ylmethyl)-2-methyl-1H-indole-1-propanoic Acid and Analogues," *J. Med. Chem.* 29:342-346, American Chemical Society, United States (1986).

(Continued)

*Primary Examiner* — Shirley V Gembeh
(74) *Attorney, Agent, or Firm* — Sterne, Kessler, Goldstein & Fox P.L.L.C.

(57) ABSTRACT

The invention relates to a polymorphic form of [5-fluoro-3-({2-[(4-fluorobenzene)sulfonyl]pyridin-3-yl}methyl)-2-methylindol-1-yl]-acetic acid which has higher solubility than other forms and is therefore useful for preparing stable pharmaceutical formulations.

16 Claims, 17 Drawing Sheets

(56) References Cited

U.S. PATENT DOCUMENTS

| | | | |
|---|---|---|---|
| 8,703,956 | B2 | 4/2014 | Betancourt et al. |
| 8,980,918 | B2 | 3/2015 | Betancourt et al. |
| 8,980,927 | B2 | 3/2015 | Armer et al. |
| 9,102,658 | B2 | 8/2015 | Tonnel et al. |
| 2001/0044437 | A1 | 11/2001 | Robinson et al. |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2007/0232681 | A1 | 10/2007 | Middlemiss et al. |
| 2008/0027092 | A1 | 1/2008 | Bonnert et al. |
| 2008/0132574 | A1 | 6/2008 | Nakade et al. |
| 2008/0255100 | A1 | 10/2008 | Bennani et al. |
| 2008/0306109 | A1 | 12/2008 | Hynd et al. |
| 2009/0030014 | A1 | 1/2009 | Kugimiya et al. |
| 2009/0163518 | A1 | 6/2009 | Bonnert |
| 2009/0170897 | A1 | 7/2009 | Corradini et al. |
| 2009/0186923 | A1 | 7/2009 | Armer et al. |
| 2009/0192195 | A1 | 7/2009 | Armer et al. |
| 2009/0286825 | A1 | 11/2009 | Wang |
| 2010/0004240 | A1 | 1/2010 | Giblin et al. |
| 2010/0016371 | A1 | 1/2010 | Giblin et al. |
| 2010/0016389 | A1 | 1/2010 | Bennani et al. |
| 2010/0022613 | A1 | 1/2010 | Armer et al. |
| 2010/0035956 | A1 | 2/2010 | Armer et al. |
| 2010/0041699 | A1 | 2/2010 | Boyd et al. |
| 2010/0056544 | A1 | 3/2010 | Lovell |
| 2010/0063103 | A1 | 3/2010 | Armer et al. |
| 2010/0266535 | A1 | 10/2010 | Armer et al. |

FOREIGN PATENT DOCUMENTS

| | | |
|---|---|---|
| EP | 0 984 012 A2 | 3/2000 |
| EP | 1 170 594 A2 | 1/2002 |
| EP | 1 211 513 A1 | 6/2002 |
| GB | 1 356 834 | 7/1974 |
| GB | 2 422 829 A | 8/2006 |
| GB | 2 422 830 A | 8/2006 |
| GB | 2 422 831 A | 8/2006 |
| JP | 2001-247570 A | 9/2001 |
| WO | WO 2003/066047 A1 | 8/2003 |
| WO | WO 2005/040114 A1 | 5/2005 |
| WO | WO 2005/044260 A1 | 5/2005 |
| WO | WO 2005/102388 A1 | 11/2005 |
| WO | WO 2005/121141 A1 | 12/2005 |
| WO | WO 2006/092579 A1 | 9/2006 |
| WO | WO 2006/095183 A1 | 9/2006 |
| WO | WO 2007/010964 A1 | 1/2007 |
| WO | WO 2007/019675 A1 | 2/2007 |
| WO | WO 2007/107772 A1 | 9/2007 |
| WO | WO 2008/012511 A1 | 1/2008 |
| WO | WO 2009/037503 A2 | 3/2009 |
| WO | WO 2009/063202 A2 | 5/2009 |
| WO | WO 2009/063215 A2 | 5/2009 |
| WO | WO 2009/077728 A1 | 6/2009 |
| WO | WO 2009/090399 A1 | 7/2009 |
| WO | WO 2009/090414 A1 | 7/2009 |
| WO | WO 2009/093026 A1 | 7/2009 |
| WO | WO 2010/008864 A2 | 1/2010 |
| WO | WO 2013/088108 A1 * | 6/2013 |
| WO | WO 2013/088109 A1 | 6/2013 |
| WO | WO 2015/092372 A1 | 6/2015 |
| WO | WO 2015/166274 A1 | 11/2015 |
| WO | WO 2015/166278 A1 | 11/2015 |

OTHER PUBLICATIONS

Emery, D.L., et al., "Prostaglandin $D_2$ causes accumulation of eosinophils in the lumen of the dog trachea," *J. Appl. Physiol.* 67(3):959-962, American Physiological Society, United States (1989).

Fujitani, Y., et al., "Pronounced Eosinophilic Lung Inflammation and Th2 Cytokine Release in Human Lipcalin-Type Prostaglandin D Synthase Transgenic Mice," *The Journal of Immunology* 168:443-449, The American Association of Immunologists, United States (2002).

Gervais, F.G., et al., "Selective modulation of chemokinesis, degranulation, and apoptosis in eosinophils through the $PGD_2$ receptors CRTH2 and DP," *J Allergy Clin Immunol* 108:982-988, Mosby, Inc., United States (2001).

Gillard, J.W., et al., "Indole 2-Propanoic Acids: The Medicinal Chemistry of L-655,240 a Potent, Non-Prostanoid Thromboxane Antagonist," *Abstr. Pap. Am. Chem. Soc.*, 195 Meeting, 327 Orgn, Accession No. 1988-34179 DDFUCPE, 1 page (1988).

Han, J., "Advances in Characterization of Pharmaceutical Hydrates," *Trends in Bio/Pharmaceutical Industry* 3:25-29, (2006).

Hardy, C.C., et al., "The Bronchoconstrictor Effect of Inhaled Prostaglandin $D_2$ in Normal and Asthmatic Men," *The New England Journal of Medicine* 311(4):209-213, Massachusetts Medical Society, United States (1984).

Hirai, H., et al., "Prostaglandin D2 Selectively Induces Chemotaxis in T Helper Type 2 Cells, Eosinophils, and Basophils via Seven-Transmembrane Receptor CRTH2," *J. Exp. Med.* 193(2):255-261, The Rockefeller University Press, United States (2001).

International Search Report for International Application No. PCT/GB2015/051296, European Patent Office, Netherlands, dated Jul. 6, 2015, 2 pages.

Johnson, M.G., et al., "Indole-phenylacetic acid inhibitors of CRTH2," Abstracts of Papers, 235$^{th}$ ACS National Meeting, Apr. 6-10, 2008, Accession No. 2008:389618 Caplus, 1 page (2008).

Kumar, S., et al., "Novel indium-mediated ternary reactions between indole-3-carboxaldehydes-allyl bromide-enamines: facile synthesis of bisindolyl- and indoyl-heterocyclic alkanes," *Tetrahedron Letters* 44:2101-2104, Elsevier Science Ltd., England (2003).

Matassa, V.G., et al., "Evolution of a Series of Peptidoleukotriene Antagonists: Synthesis and Structure/Activity Relationships of 1,3,5-Substituted Indoles and Indazoles," *J. Med. Chem.* 33:1781-1790, American Chemical Society, United States (1990).

Mathiesen, J.M., et al., "Identification of Indole Derivatives Exclusively Interfering with a G Protein-Independent Signaling Pathway of the Prostaglandin D2 Receptor CRTH2," *Mol Pharmacol* 68:393-402, American Society for Pharmacology and Experimental Therapeutics, United States (2005).

Monneret, G., et al.,"15R-Methyl-Prostaglandin $D_2$ Is a Potent and Selective CRTH2/$DP_2$ Receptor Agonist in Human Eosinophils," *The Journal of Pharmacology and Experimental Therapeutics* 304(1):349-355, The American Society for Pharmacology and Experimental Therapeutics, United States (2003).

Murray, J.J., et al., "Release of Prostaglandin $D_2$ Into Human Airways During Acute Antigen Challenge," *The New England Journal of Medicine* 315(13):800-804, Massachusetts Medical Society, United States (1986).

Patent Abstracts of Japan, English language abstract of JP 2001-247570, (2001) (listed as document FP5 on accompanying form PTO/SB/08A).

Royer, J.F., et al., "A novel antagonist of prostaglandin $D_2$ blocks the locomotion of eosinophils and basophils," *Eur J Clin Invest* 38(9):663-671, European Society for Clinical Investigation, The Netherlands (2008).

Sampson, S.E., et al., "Effect of inhaled prostaglandin $D_2$ in normal and atopic subjects, and of pretreatment with leukotriene $D_4$," *Thorax* 52:513-518, British Medical Assn, England (1997).

"Prodrugs: Challenges and Rewards Part 1," in *Biotechnology: Pharmaceutical Aspects*, Stella, V.J., et al., eds., p. 24, American Association of Pharmaceutical Scientists, United States (2007).

Vippagunta, S.R., et al., "Crystalline solids," *Advanced Drug Delivery Reviews* 48:3-26, Elsevier Science B.V., Netherlands (2001).

Werz, O. and Steinhilber, D., "Pharmacological intervention with 5-lipoxygenase: New insights and novel compounds," *Expert Opinion on Therapeutic Patents* 15(5):505-519, Accession No. 2005230213 EMBASE, 1 page (2005).

"Chapter 2 Drug Design and Relationship of Functional Groups to Pharmacological Activity," in *Foye's Principles of Medicinal Chemistry Fifth Edition*, Williams, D.A. and Lemke, T.L., eds., Lippincott Williams & Wilkins, United States (2002).

Braga, D., et al., "Crystal Polymorphism and Multiple Crystal Forms," *Struct. Bond.* 132:25-50, Springer-Verlag, United States (2009).

(56) References Cited

OTHER PUBLICATIONS

Pettipher, R., et al., "Heightened response of eosinophilic asthmatic patients to the CRTH2 antagonist OC000459," *Allergy* 69:1223-1232, John Wiley & Sons Ltd., United Kingdom (2014).

* cited by examiner

POLYMORPHIC FORM OF [5-FLUORO-3-({2-[(4-FLUOROBENZENE) SULFONYL] PYRIDIN-3-YL}METHYL)-2-METHYLINDOL-1-YL]-ACETIC ACID

The present invention relates to a novel polymorphic form of a compound which is useful as a pharmaceutical, to methods for preparing this polymorph, compositions containing it and its use in the treatment and prevention of allergic diseases such as asthma, allergic rhinitis and atopic dermatitis and other inflammatory diseases mediated by prostaglandin $D_2$ ($PGD_2$) or other agonists acting at the CRTH2 receptor on cells including eosinophils, basophils and Th2 lymphocytes.

$PGD_2$ is an eicosanoid, a class of chemical mediator synthesised by cells in response to local tissue damage, normal stimuli or hormonal stimuli or via cellular activation pathways. Eicosanoids bind to specific cell surface receptors on a wide variety of tissues throughout the body and mediate various effects in these tissues. $PGD_2$ is known to be produced by mast cells, macrophages and Th2 lymphocytes and has been detected in high concentrations in the airways of asthmatic patients challenged with antigen (Murray et al., (1986), *N. Engl. J. Med.* 315: 800-804). Instillation of $PGD_2$ into airways can provoke many features of the asthmatic response including bronchoconstriction (Hardy et al., (1984) *N. Engl. J. Med.* 311: 209-213; Sampson et al., (1997) *Thorax* 52: 513-518) and eosinophil accumulation (Emery et al., (1989) *J. Appl. Physiol.* 67: 959-962).

The potential of exogenously applied $PGD_2$ to induce inflammatory responses has been confirmed by the use of transgenic mice overexpressing human $PGD_2$ synthase which exhibit exaggerated eosinophilic lung inflammation and Th2 cytokine production in response to antigen (Fujitani et al., (2002) *J. Immunol.* 168: 443-449).

The first receptor specific for $PGD_2$ to be discovered was the DP receptor which is linked to elevation of the intracellular levels of cAMP. However, $PGD_2$ is thought to mediate much of its proinflammatory activity through interaction with a G protein-coupled receptor termed CRTH2 (chemoattractant receptor-homologous molecule expressed on Th2 cells) which is expressed by Th2 lymphocytes, eosinophils and basophils (Hirai et al., (2001) *J. Exp. Med.* 193: 255-261, and EP0851030 and EP-A-1211513 and Bauer et al., EP-A-1170594). It seems clear that the effect of $PGD_2$ on the activation of Th2 lymphocytes and eosinophils is mediated through CRTH2 since the selective CRTH2 agonists 13,14 dihydro-15-keto-$PGD_2$ (DK-$PGD_2$) and 15R-methyl-$PGD_2$ can elicit this response and the effects of $PGD_2$ are blocked by an anti-CRTH2 antibody (Hirai et al., 2001; Monneret et al., (2003) *J. Pharmacol. Exp. Ther.* 304: 349-355). In contrast, the selective DP agonist BW245C does not promote migration of Th2 lymphocytes or eosinophils (Hirai et al., 2001; Gervais et al., (2001) *J. Allergy Clin. Immunol.* 108: 982-988). Based on this evidence, antagonising $PGD_2$ at the CRTH2 receptor is an attractive approach to treat the inflammatory component of Th2-dependent allergic diseases such as asthma, allergic rhinitis and atopic dermatitis.

EP-A-1170594 suggests that the method to which it relates can be used to identify compounds which are of use in the treatment of allergic asthma, atopic dermatitis, allergic rhinitis, autoimmune, reperfusion injury and a number of inflammatory conditions, all of which are mediated by the action of $PGD_2$ or other agonists at the CRTH2 receptor.

Since the publication of EP-A-1170594, there have been a great many publications relating to compounds having CRTH2 antagonist activity.

In our earlier applications WO-A-2005/044260, WO2006/095183 and WO2008/012511 we describe compounds which are antagonists of $PGD_2$ at the CRTH2 receptor. These compounds are indole-1-acetic acid derivatives substituted at the 3-position with a CH2-aryl group which may be substituted with one or more further substituents. The compounds described in these documents are potent antagonists in vitro of $PGD_2$ at the CRTH2 receptor.

Our earlier application WO2009/090414 relates to pyridyl analogues of the compounds of WO2008/012511. Surprisingly, it has been found that specific pyridyl regioisomers and substitution thereof give rise to an optimal balance of potency and pharmacokinetic properties. Specifically it has been found that the introduction of a phenyl sulfonyl substituent onto the 2-position of the pyridin-3-yl regioisomer provides compounds with good potency in a functional in vitro assay together with good pharmacokinetics in vivo.

The compounds described in WO2009/090414 are, as predicted, useful in the treatment of diseases and conditions mediated by the action of $PGD_2$ at the CRTH2 receptor. One of these compounds, [5-fluoro-3-({2-[(4-fluorobnzene)sulfonyl]pyridin-3-yl}methyl)-2-methylindol-1-yl]-acetic acid (Compound 1) is particularly useful.

A method for the synthesis of [5-fluoro-3-({2-[(4-fluorobenzene)sulfonyl]pyridin-3-yl}methyl)-2-methylindol-1-yl]-acetic acid is set out in WO2009/090414 but the present inventors found that batches of compound produced by this method are amorphous.

Crystalline forms are often more stable than amorphous forms and so an amorphous form may spontaneously convert to a crystalline form over time. This is clearly a disadvantage in the case of pharmaceutically active compounds as different forms of a compound may have different pharmacokinetic properties. Therefore, the inventors set out to develop a crystalline form of Compound 1.

The inventors also sought to prepare a crystalline form of a non-solvated form of Compound 1. Non-solvated forms are often more suitable for the preparation of pharmaceutical compositions as many solvates are thermodynamically unstable at ambient temperature, although hydrates are generally preferred to other solvates.

[5-fluoro-3-({2-[(4-fluorobenzene)sulfonyl]pyridin-3-yl}methyl)-2-methylindol-1-yl]-acetic acid was found by the present inventors to be enantiotropic and thus the stable polymorphic form of the compound depends upon the temperature. The inventors found three different polymorphic forms of this compound: a first, designated Form 1, which is thermodynamically stable at high temperatures, although the exact transition temperature was difficult to determine; a second (designated Form 2) which is thermodynamically stable at temperatures up to about 60-65° C.; and a third form (Form 3) which is stable at temperatures between the stability ranges of Forms 2 and 1.

The third polymorphic form, although not the most thermodynamically stable form at room temperature and has the advantage of having a higher solubility than Form 1 and Form 2 It is therefore an highly advantageous form of Compound 1.

Therefore, in a first aspect of the present invention, there is provided a polymorphic form of [5-fluoro-3-({2-[(4-fluorobenzene)sulfonyl]pyridin-3-yl}methyl)-2-methylindol-1-yl]-acetic acid (Compound 1), characterised in that it gives an FT-Raman spectrum which is characterised by peaks at 3068±2 cm$^{-1}$, 3054±2 cm$^{-1}$, 2976±2 cm$^{-1}$, 1582±2 cm⁻¹, 1427±2 cm⁻¹, 1298±2 cm⁻¹, 1213±2 cm⁻¹, 1190±2 cm⁻¹, 1164±2 cm⁻¹, 1060±2 cm⁻¹, 956±2 cm⁻¹, 927±2 cm⁻¹, 834±2 cm⁻¹, 700±2 cm⁻¹, 502±2 cm⁻¹, 421±2 cm⁻¹, 401±2 cm⁻¹, 388±2 cm⁻¹, 363±2 cm⁻¹, 353±2 cm⁻¹, 301±2 cm⁻¹, 208±2 cm⁻¹, 116±2 cm⁻¹.

The complete Raman spectrum for Polymorphic Form 3 of Compound 1 is characterised by peaks at 3086±2 cm⁻¹, 3068±2 cm⁻¹, 3054±2 cm⁻¹, 2976±2 cm⁻¹, 2940±2 cm⁻¹, 2919±2 cm⁻¹, 2757±2 cm⁻¹, 1629±2 cm⁻¹, 1582±2 cm⁻¹, 1571±2 cm⁻¹, 1485±2 cm⁻¹, 1463±2 cm⁻¹, 1451±2 cm⁻¹, 1427±2 cm⁻¹, 1384±2 cm⁻¹, 1355±2 cm⁻¹, 1311±2 cm⁻¹, 1298±2 cm⁻¹, 1213±2 cm⁻¹, 1190±2 cm⁻¹, 1164±2 cm⁻¹, 1152±2 cm⁻¹, 1131±2 cm⁻¹, 1094±2 cm⁻¹, 1060±2 cm⁻¹, 1021±2 cm⁻¹, 956±2 cm⁻¹, 927±2 cm⁻¹, 908±2 cm⁻¹, 882±2 cm⁻¹, 834±2 cm⁻¹, 824±2 cm⁻¹, 773±2 cm⁻¹, 728±2 cm⁻¹, 717±2 cm⁻¹, 700±2 cm⁻¹, 674±2 cm⁻¹, 655±2 cm⁻¹, 630±2 cm⁻¹, 586±2 cm⁻¹, 569±2 cm⁻¹, 539±2 cm⁻¹, 502±2 cm⁻¹, 444±2 cm⁻¹, 421±2 cm⁻¹, 401±2 cm⁻¹, 388±2 cm⁻¹, 363±2 cm⁻¹, 353±2 cm⁻¹, 301±2 cm⁻¹, 279±2 cm⁻¹, 234±2 cm⁻¹, 208±2 cm⁻¹, 170±2 cm⁻¹, 116±2 cm⁻¹;

where the signals which are underlined are those which differ from the signals in the other polymorphic forms of Compound 1 by at least 2 cm⁻¹.

This polymorphic form (known as Form 3) is thermodynamically stable at temperatures above about 60-65° C. Furthermore, Form 3 is the most soluble crystalline form of Compound 1 in both fasted state and fed state simulated intestinal fluid and this may prove advantageous both for formulation purposes and for its bioavailability in vivo.

It has also been found that Polymorphic Form 3 of Compound 1, optionally in admixture with Polymorphic Form 2, is a useful starting material for the preparation of pure Polymorphic Form 2.

Polymorphic Form 3 has a melting signal at 200° C. as measured by differential scanning calorimetry and is stable at temperatures above about 60-65° C. Below this temperature, Form 2 is the thermodynamically more stable form, with Form 1 being the thermodynamically stable form at very high temperatures, although it is difficult to determine a transition temperature between Forms 2 and 3 as the measurement is usually carried out using a suspension equilibration experiment with a mixture of the different forms of Compound 1 and, in this experiment, Compound 1 appears to decompose before the transition temperature is reached.

Suitably, Polymorphic Form 3 of Compound 1 will be pure or substantially pure. Thus, it will usually comprise not more than 10% of other forms of Compound 1, preferably not more than 5%, more preferably not more than 2% and most preferably not more than 1% of other forms of Compound 1. The other forms of Compound 1 may be the amorphous form or Forms 1 or 3.

It is also preferred that the Polymorphic Form 3 of Compound 1 is substantially free of other impurities, for example traces of solvent. Therefore, suitably, the Polymorphic Form 2 of compound 1 comprises not more than 1% by weight of solvent (e.g. methylethylketone). More suitably it comprises not more than 0.5% by weight preferably not more than 0.2% and more preferably not more than 0.1% by weight.

A method for the preparation of Compound 1 is set out in WO2009/090414. However, as already discussed, the method described appears to lead to an amorphous form of the compound. Recrystallisation of this product gave rise to polymorphic Form 1.

Polymorphic Form 3 may be prepared from the product described in WO2009/090414 by phase equilibration for a prolonged period, typically 15 to 30 days at room temperature in methylethylketone. In some cases, Polymorphic form 2 is obtained in admixture with polymorphic form, Form 3.

Therefore, where necessary, Polymorphic Form 3 may be obtained from a mixture of Forms 2 and 3 by further phase equilibration in methylethylketone at elevated temperature, typically 60 to 80° C., but more usually at 65 to 80° C. and typically 70-75° C., for a period of about 20-36 hours, but suitably 24-26 hours.

If a still purer product is required, the process may comprise seeding a saturated solution of Compound 1 in methylethyletone at an elevated temperature of about 65 to 80° C., more usually 70-75° C., with crystals of Polymorphic Form 3 obtained from the step above and allowing crystallisation to take place, followed by isolating the crystals of polymorphic Form 3.

Therefore, in a further aspect of the invention there is provided a process for the preparation of Polymorphic form 2 of [5-fluoro-3-({2-[(4-fluorobenzene)sulfonyl]pyridin-3-yl}methyl)-2-methylindol-1-yl]-acetic acid as defined above, the process comprising:

a. suspending [5-fluoro-3-({2-[(4-fluorobenzene)sulfonyl] pyridin-3-yl}methyl)-2-methylindol-1-yl]-acetic acid in methylethylketone;

b. stirring the suspension at a temperature of about 15 to 25° C. for 15 to 30 days; and c. isolating and drying the crystalline [5-fluoro-3-({2-[(4-fluorobenzene)sulfonyl] pyridin-3-yl}methyl)-2-methylindol-1-yl]-acetic acid.

After this process is carried out, the product will generally be a mixture of Polymorphic Forms 2 and 3.

Therefore, the process may further comprise the steps of:

d. dissolving the product of step (c) in methyl ethyl ketone at an elevated temperature of from about 65 to 80° C. to obtain a saturated solution;

e. partially evaporating the solvent;

f. stirring the mixture for 20-36 hours such that crystallisation takes place; and g. isolating the crystalline Compound 1.

Optionally, the process may comprise the additional steps of:

h. preparing a saturated solution of Compound 1 in methylethylketone at an elevated temperature of about 65-80° C.;

i. seeding the solution with the crystalline product of step (g);

j. allowing crystallisation to take place and;

k. isolating the crystalline product.

Optionally, steps (h) to (k) may be repeated using the product of step (k) as the seed crystals for the next crystallisation step.

The starting Compound 1 used in the process may be amorphous material, polymorphic Form 1 or polymorphic Form 2 mixtures of any of these. However, this process is particularly useful when starting from amorphous material, for example material obtained from the process described in WO2009/090414.

The phase equilibration is more typically carried out over about 15 to 20 days, for example 17 days.

Polymorphic Form 3 is, of course, useful as a pharmaceutical but, in addition, it has been found to be the most suitable starting material in the preparation of Polymorphic Form 2, which is the most thermodynamically stable form at temperatures up to about 65° C.

As described in our co-pending application, Polymorphic Form 2 of Compound 1 can be prepared by preparing a saturated solution of Polymorphic Form 3 of Compound 1 in acetonitrile or in a mixture of acetonitrile and water, seeding the solution with crystals of Polymorphic Form 2 and allowing crystallisation to take place.

As discussed in WO2009/090414, Compound 1 has CRTH2 antagonist activity and is therefore useful in the treatment of conditions which are mediated by $PGD_2$ or other agonists binding to CRTH2.

Thus, in a further aspect of the invention there is provided Polymorphic Form 3 of [5-fluoro-3-({2-[(4-fluorobenzene)sulfonyl] pyridin-3-yl}methyl)-2-methylindol-1-yl]-acetic acid as defined above for use in medicine, particularly in the treatment or prevention of allergic diseases, asthmatic conditions and inflammatory diseases, examples of which are asthma, asthma exacerbations, chronic obstructive pulmonary disease, allergic rhinitis conjunctivitis, nasal polyps, atopic dermatitis, contact hypersensitivity (including contact dermatitis), eosinophilic cough, eosinophilic bronchitis, eosinophilic gastroenteritis, eosinophilic oesophagitis, food allergies, inflammatory bowel disease, ulcerative colitis, Crohn's disease, mastocytosis, urticaria, hypereosinophilic syndrome, hyper IgE syndrome, fibrotic diseases, Churg-Strauss syndrome and multiple sclerosis.

The compound is also of use in the treatment of infection.

The term "asthma" includes all types of asthma, for example allergic asthma, non allergic asthma, eosinophilic asthma, steroid resistant asthma, Th2 dependent asthma, non-Th2 dependent asthma and aspirin induced asthma. In one embodiment, the asthma is allergic asthma and in another embodiment the asthma is eosinophilic asthma.

"Asthma exacerbations" includes exacerbations induced by viral infections, especially infection with respiratory syncytial virus (RSV) or rhinovirus.

Allergic rhinitis includes both perennial allergic rhinitis and seasonal allergic rhinitis.

"Conjunctivitis" includes, in particular, allergic conjunctivitis, vernal keratoconjunctivitis and atopic keratoconjunctivitis.

"Infection" includes bacterial, viral or fungal infection. The infection may occur in patients who are atopic or are at risk of becoming atopic and may be, for example a rhinovirus, influenza or RSV infection, especially in asthmatic patients. Alternatively, the infection may be a bacterial infection for example a *Staphylococcus aureus* infection, particularly in patients suffering from atopic dermatitis.

The term "fibrotic diseases" includes, in particular, fibrotic diseases caused/exacerbated by Th2 immune responses, for example idiopathic pulmonary fibrosis, scleroderma and hypertrophic scars.

Polymorph 3 of Compound 1 may also be of use in the treatment of other PGD2-mediated diseases. Diseases which may be mediated by PGD2 include autoimmune diseases such as systemic lupus erythematus, psoriasis, acne, allograft rejection, rheumatoid arthritis, psoriatic arthritis and osteoarthritis.

The invention further provides a method for the treatment or prevention of a disease or condition selected from those listed above, the method comprising administering to a patient in need of such treatment an effective amount of Polymorphic Form 3 of Compound 1 as defined above.

The patient will be a mammal, for example a human.

There is also provided the use of Polymorphic Form 3 of Compound 1 as defined above in the preparation of an agent for the treatment or prevention of a disease or condition selected from those listed above.

Polymorphic Form 3 of [5-fluoro-3-({2-[(4-fluorobenzene)sulfonyl] pyridin-3-yl}methyl)-2-methylindol-1-yl]-acetic acid must be formulated in an appropriate manner depending upon the diseases or conditions it is required to treat.

Therefore, in a further aspect of the invention there is provided a pharmaceutical or veterinary composition comprising Polymorphic Form 3 of [5-fluoro-3-({2-[(4-fluorobenzene)sulfonyl] pyridin-3-yl}methyl)-2-methylindol-1-yl]-acetic acid as defined above together with a pharmaceutically or veterinarily acceptable excipient. Other active materials may also be present, as may be considered appropriate or advisable for the disease or condition being treated or prevented.

The excipient, or, if more than one be present, each of the excipients, must be acceptable in the sense of being compatible with the other ingredients of the formulation and not deleterious to the recipient.

The formulations include those suitable for oral (including viscous oral formulations), rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association Polymorphic Form 3 of [5-fluoro-3-({2-[(4-fluorobenzene)sulfonyl] pyridin-3-yl}methyl)-2-methylindol-1-yl]-acetic acid with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing Polymorphic Form 3 of [5-fluoro-3-({2-[(4-fluorobenzene)sulfonyl] pyridin-3-yl}methyl)-2-methylindol-1-yl]-acetic acid in conjunction or association with a pharmaceutically or veterinarily acceptable excipient.

Formulations for oral administration in the present invention may be presented as: discrete units such as capsules, sachets, tablets, troches or lozenges each containing a predetermined amount of Polymorph 2 of Compound 1; as a powder or granules; as a solution or a suspension of the active agent in an aqueous liquid or a non-aqueous liquid; or as an oil-in-water liquid emulsion or a water in oil liquid emulsion; or as a syrup or elixir; or as a bolus, etc.

For compositions for oral administration (e.g. tablets, capsules, formulations comprising a mucoadherent etc), the term "acceptable carrier" includes vehicles such as common excipients e.g. binding agents, for example syrup, acacia, gelatin, sorbitol, tragacanth, polyvinylpyrrolidone (povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; wetting agents/surfactants such as poloxamers, polysorbates, sodium docusate and sodium lauryl sulfate; disintegrants such as starch or sodium starch glycolate; and lubricants such as magnesium stearate, sodium stearate and other metallic stearates, glycerol stearate, stearic acid, silicone fluid, talc waxes, oils and colloidal silica. Sweetening agents and flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine Polymorphic Form 3 of Compound 1 in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Some formulations may comprise a mucoadherent, for example a mucopolysaccharide such as sodium hyaluronate. Such compositions may be formulated as, for example, liquids, liquid syrups, soft gels, liquid gels, flowable gels or aqueous suspensions and may, in addition to the active agent and the mucoadherent, also contain one or more additional excipients as set out above. Liquid formulations will usually also contain a liquid carrier, which may be a solvent or suspending agent, for example water or saline solution and may also contain a substance to increase their viscosity, for example sodium carboxymethylcellulose, sorbitol or dextran.

Other formulations suitable for oral administration include lozenges comprising the active agent in a flavoured base, usually sucrose and acacia or tragacanth; pastilles comprising Polymorphic Form 3 of Compound 1 in an inert base such as gelatin and glycerin, or sucrose and acacia; and mouthwashes comprising the active agent in a suitable liquid carrier.

For topical application to the skin, the composition may be made up into a cream, ointment, jelly, solution or suspension etc. Cream or ointment formulations that may be used for Polymorphic Form 3 of Compound 1 are conventional formulations well known in the art, for example, as described in standard text books of pharmaceutics such as the British Pharmacopoeia.

The composition defined above may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties include dry powder inhalers and metered dose inhalers. Dry powder inhalers usually contain, in addition to Polymorphic Form 3 of Compound 1, a suitable carrier such lactose and, if desired, adjuncts, such as surfactants and/or diluents and/or flow aids and/or lubricants. Metered dose inhalers for dispersing powders usually contain, in addition to the Polymorphic Form 3 of Compound 1, a liquid propellant with a boiling point below room temperature and, if desired, adjuncts, such as liquid or solid non-ionic or anionic surfactants and/or diluents. Pharmaceutical compositions for treatment of the respiratory tract in which the pharmacologically active ingredient is in solution (e.g., either solution for nebulisation or metered dose inhalers) contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of Compound 1 will be about 0.01 to 100 mg/kg; so as to maintain the concentration of drug in the plasma at a concentration effective to inhibit $PGD_2$ at the CRTH2 receptor. The precise amount of Compound 1 which is therapeutically effective, and the route by which such compound is best administered, is readily determined by one of ordinary skill in the art by comparing the blood level of the agent to the concentration required to have a therapeutic effect.

The pharmaceutical composition is most suitably formulated as a once-a-day administration, although more frequent dosing may be used in some cases, for example twice, three times or four times daily dosing. On the other hand, it may sometimes be possible to dose less frequently than once daily, for example once every two days. In some circumstances a dosage regimen may be used in which the composition is administered for a first period and then, during a second period, administration ceases or, alternatively, the composition administered at a lower dose. Such a dosage regimen is described in WO 2009/063202.

Polymorphic Form 3 of Compound 1 as defined above may be used in combination with one or more active agents which are useful in the treatment of the diseases and conditions listed above, although these active agents are not necessarily inhibitors of $PGD_2$ at the CRTH2 receptor.

Therefore, the pharmaceutical composition described above may additionally contain one or more of these active agents.

There is also provided the use of Polymorphic Form 3 of Compound 1 as defined above in the preparation of an agent for the treatment of diseases and conditions mediated by CRTH2 receptor agonists, especially $PGD_2$, wherein the agent also comprises an additional active agent useful for the treatment of the same diseases and conditions.

These additional active agents may be other CRTH2 receptor antagonists or may have a completely different mode of action. They include existing therapies for allergic and other inflammatory diseases including:

Suplatast tosylate and similar compounds;

β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline and aminophylline, mast cell stabilisers such as sodium cromoglycate or muscarinic receptor antagonists such as tiotropium;

antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;

$\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;

modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;

Leukotriene antagonists such as montelukast, pranlukast and zafirlukast leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-sub stituted-2-cyanonaphthalene compounds such as L-739010, 2-cyanoquinoline compounds such as L-746, 530, indole and quinoline compounds such as MK-591, MK-886 and BAY x 1005;

Phosphdiesterase inhibitors, including PDE4 inhibitors such as roflumilast;

anti-IgE antibody therapies such as omalizumab;

anti-infectives such as fusidic acid (particularly for the treatment of atopic dermatitis);

anti-fungals such as clotrimazole (particularly for the treatment of atopic dermatitis);

immunosuppressants such as tacrolimus and particularly pimecrolimus in the case of inflammatory skin disease or alternatively FK-506, rapamycin, cyclosporine, azathioprine or methotrexate;

Immunotherapy agents including allergen immunotherapy such as Grazax;

corticosteroids such as prednisone, prednisolone, flunisolide, triamcinolone acetonide, beclomethasone dipropionate, budesonide, fluticasone propionate mometasone furoate and fluticasone furoate drugs which promote Th1 cytokine response such as interferons, TNF or GM-CSF.

CRTH2 antagonists may also be combined with therapies that are in development for inflammatory indications including:

other antagonists of $PGD_2$ acting at other receptors such as DP antagonists;

drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicylates such as aspirin; COX-2 inhibitors such as meloxicam, celecoxib, rofecoxib, valdecoxib and etoricoxib, low dose methotrexate, lefunomide, ciclesonide, hydroxychloroquine, d-penicillamine, auranofin or parenteral or oral gold;

drugs that modulate the activity of Th2 cytokines IL-4 and IL-5 such as blocking monoclonal antibodies and soluble receptors;

PPAR-γ agonists such as rosiglitazone; or with anti-RSV antibodies such as Synagis (palivizumab) and agents that may be used to treat rhinovirus infection in the future e.g. intereferon-alpha, interferon-beta or other interferons.

Combinations of Polymorphic Form 3 of Compound 1 as defined above with leukotriene antagonists such as montelukast, pranlukast and zafirlukast are particularly suitable, especially combinations with montelukast.

In yet a further aspect of the invention, there is provided a product comprising Polymorphic Form 3 of Compound 1 as defined above and one or more of the agents listed above as a combined preparation for simultaneous, separate or sequential use in the treatment of a disease or condition mediated by the action of $PGD_2$ at the CRTH2 receptor.

In yet another aspect of the invention there is provided a kit for the treatment of a disease or condition mediated by the action of $PGD_2$ at the CRTH2 receptor comprising a first container comprising Polymorphic Form 3 of Compound 1 as defined above and a second container comprising one or more of the active agents listed above.

The invention will now be described in greater detail with reference to the examples and to the following drawings in which.

Figure 3:
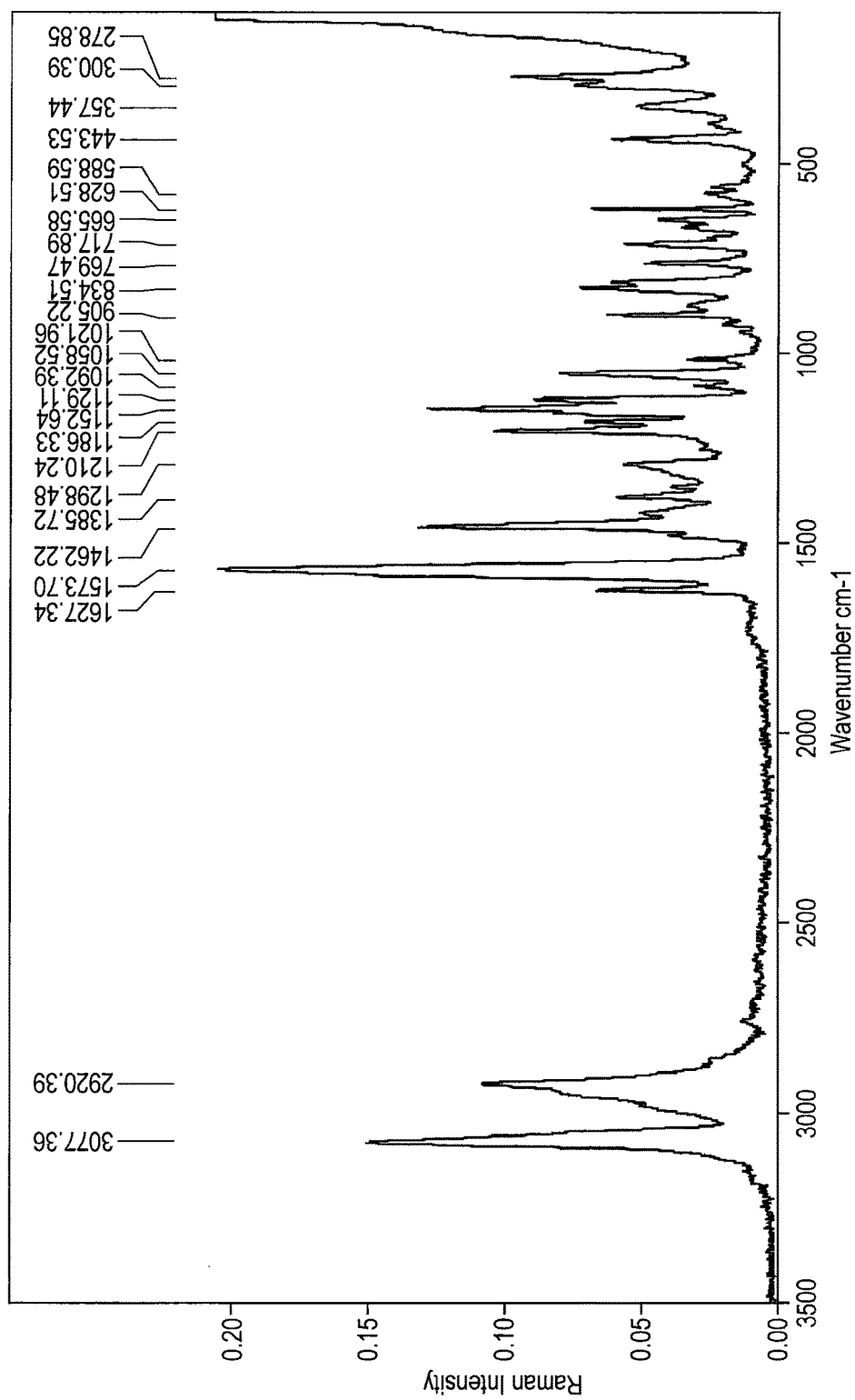

FIG. 3 shows the FT-Raman spectrum of Compound 1, Batch 3. The spectrum was used as a reference for the preliminary polymorphism study. The most pronounced Raman peaks are labeled in the figure.

Figure 4:
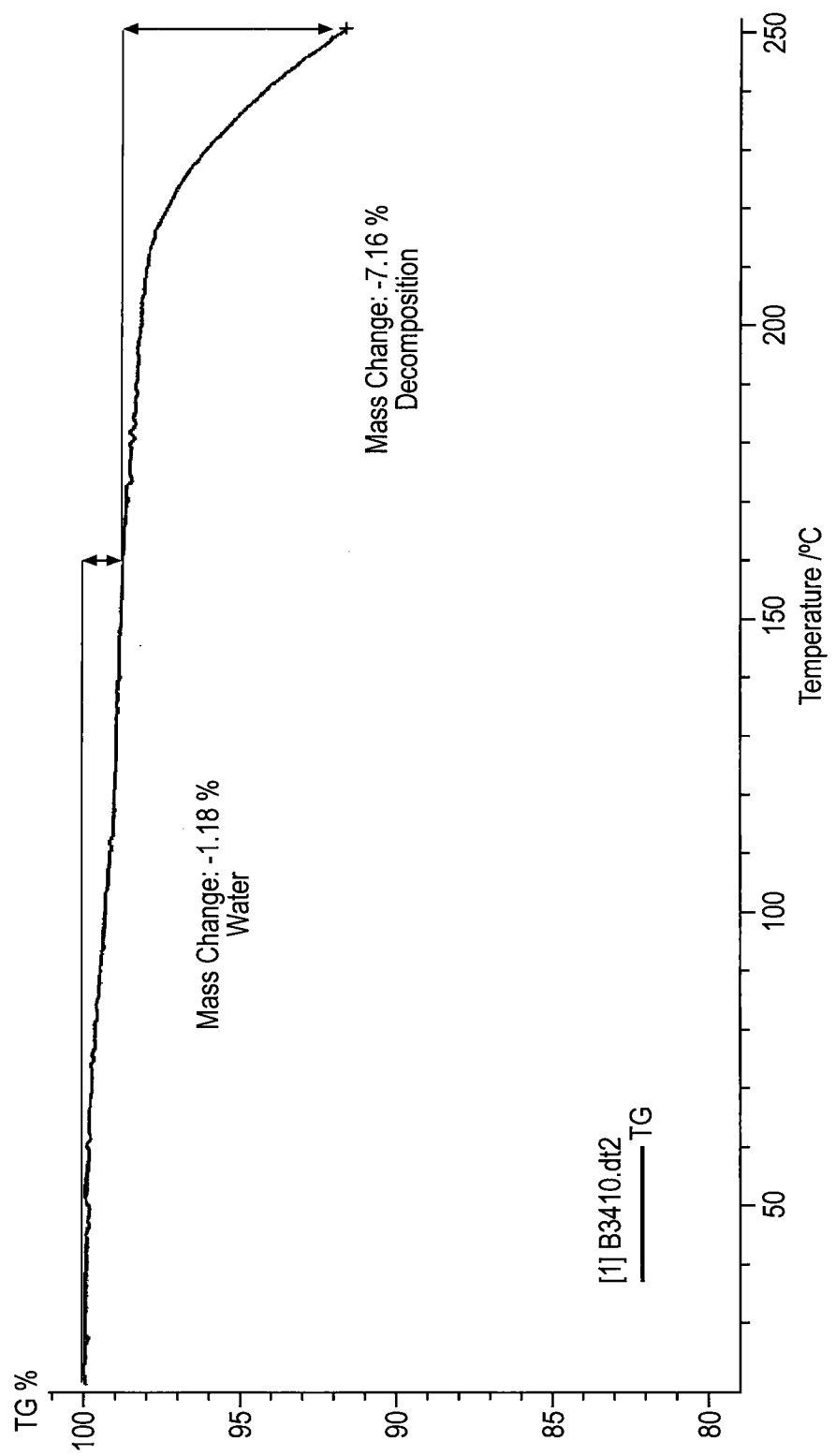

FIG. 4 shows a plot of TG-FTIR of Compound 1, Batch 3 in a temperature range of 25° C. to 250° C. and a heating rate of 10° C./min.

Figure 5:
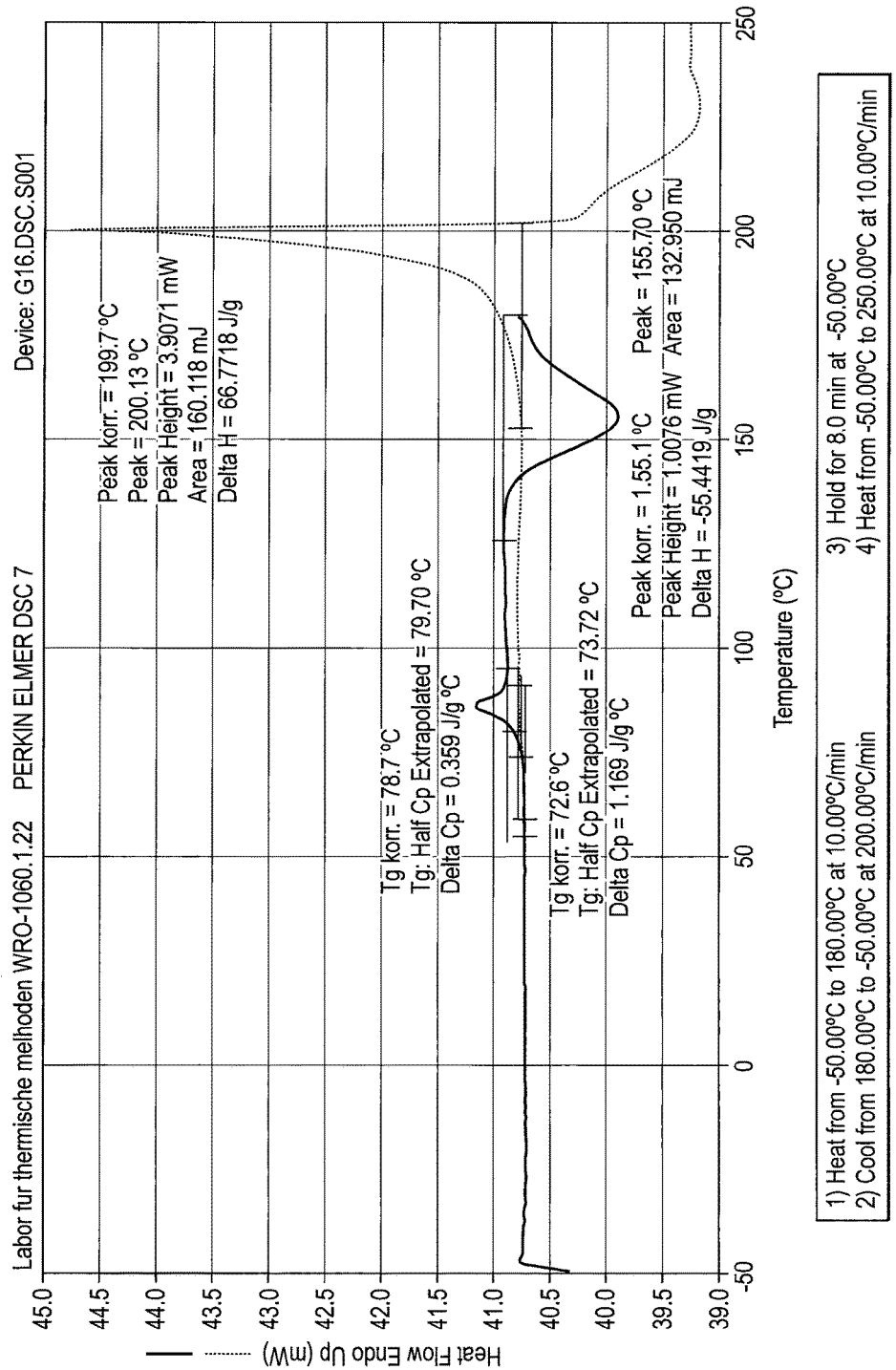

FIG. 5 is a differential scanning calorimetry trace for Compound 1, Batch 1.

Figure 6:
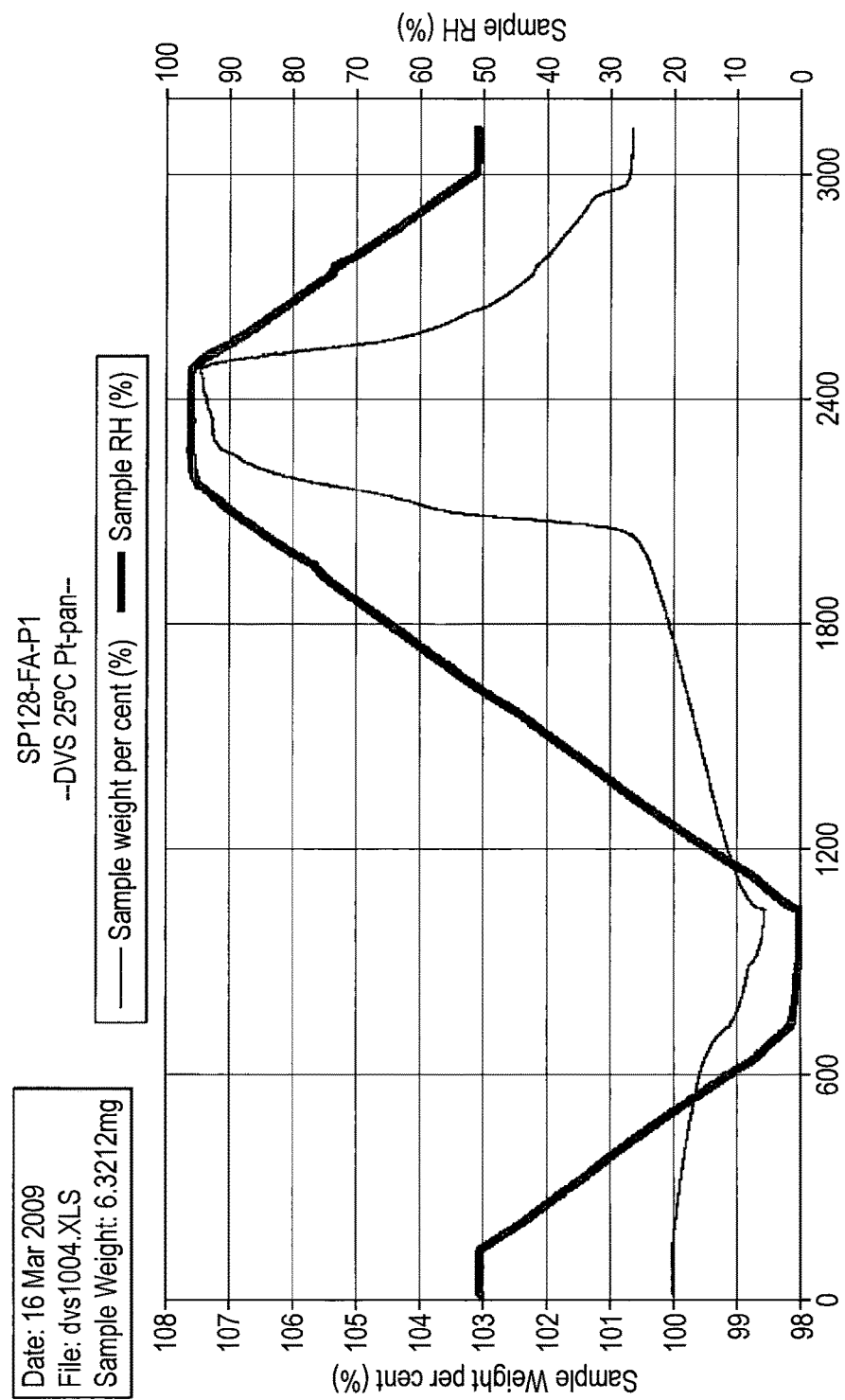

FIG. 6 is a dynamic vapour sorption curve for Compound 1, Batch 1 showing relative humidity over the sample and sample weight percent versus time.

Figure 7:
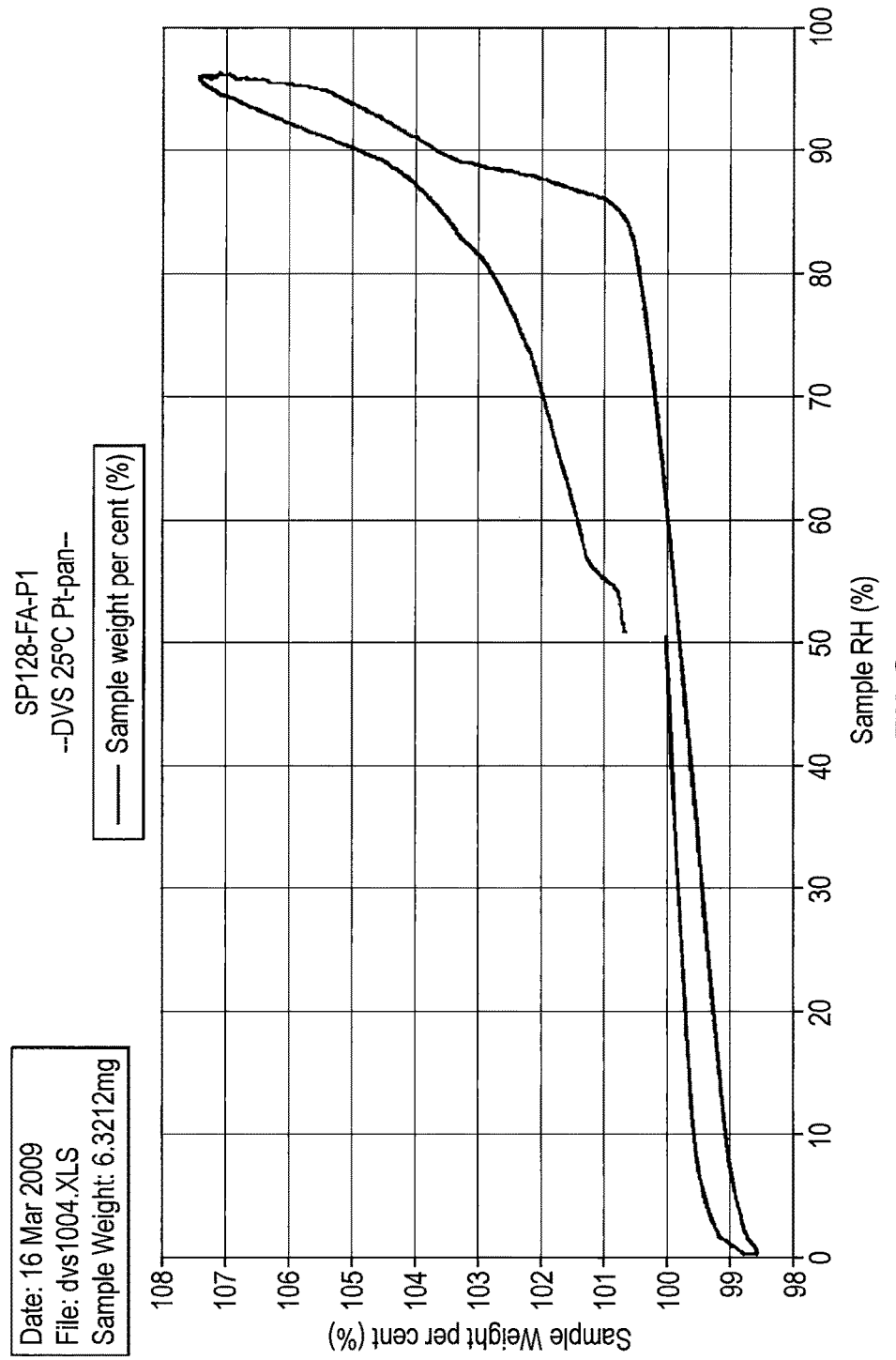

FIG. 7 is a further dynamic vapour sorption curve for Compound 1, Batch 1 showing sample weight percent against relative humidity.

Figure 8:
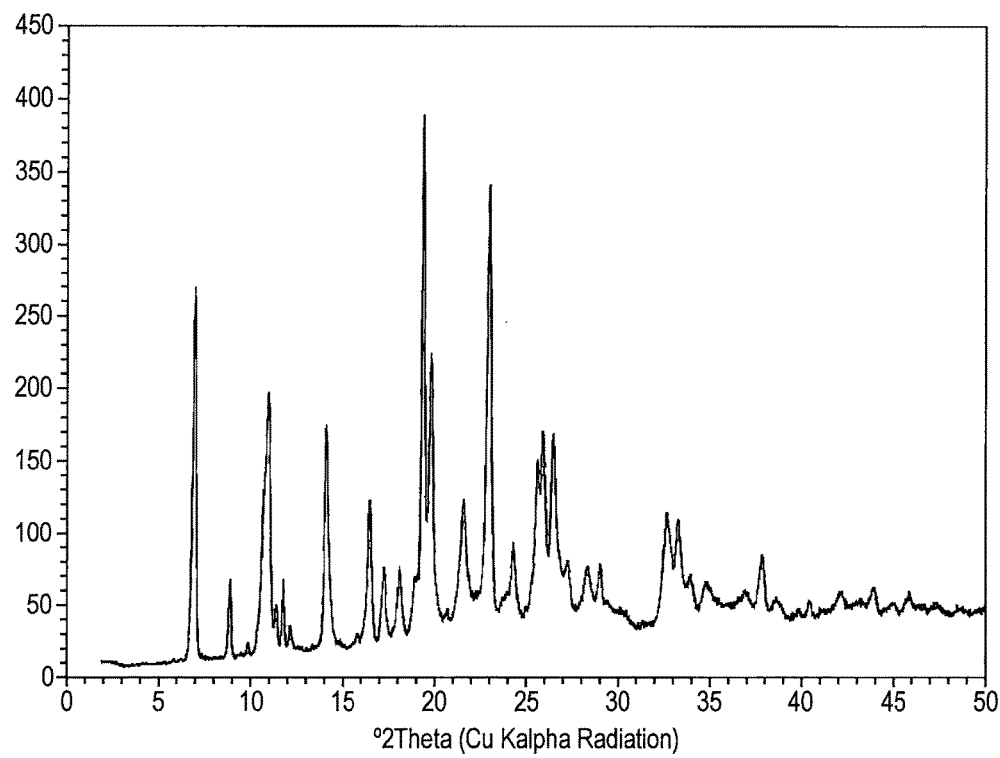

FIG. 8 shows the PXRD pattern of Compound 1, Batch 2.

Figure 9:
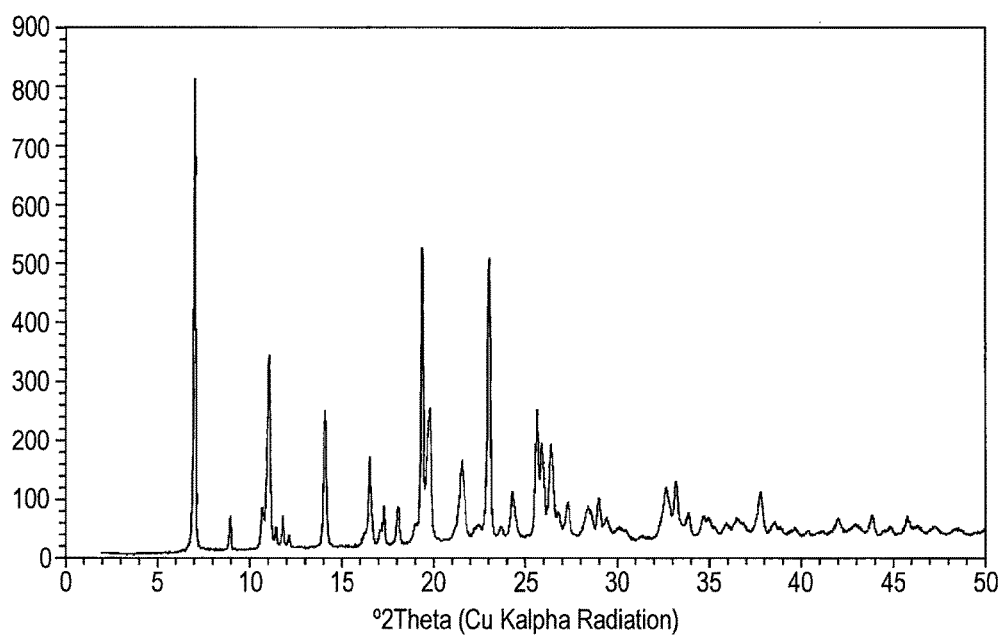

FIG. 9 shows the PXRD pattern of the product obtained by recrystallising Compound 1, Batch 1 from ethyl acetate and then drying the crystalline solid obtained (Example 3).

Figure 10:
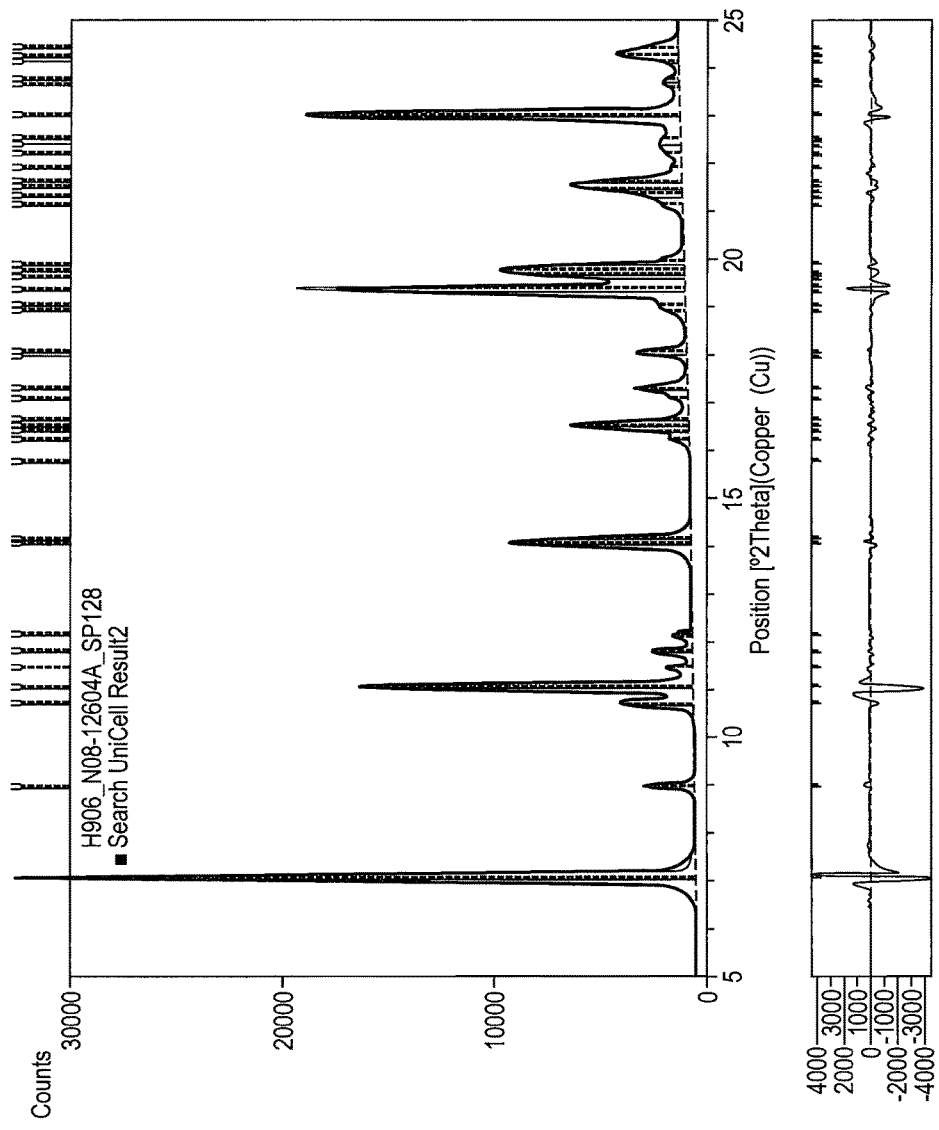

FIG. 10 is a detail of the PXRD pattern of the recrystalised and dried product from Example 3 (Polymorphic Form 1) showing the fit between the experimental pattern of the product of Example 3 (Form 1; red, file: H906) and the data calculated based upon a LeBail-fit (blue). Below is the difference plot shown in red.

Figure 11:
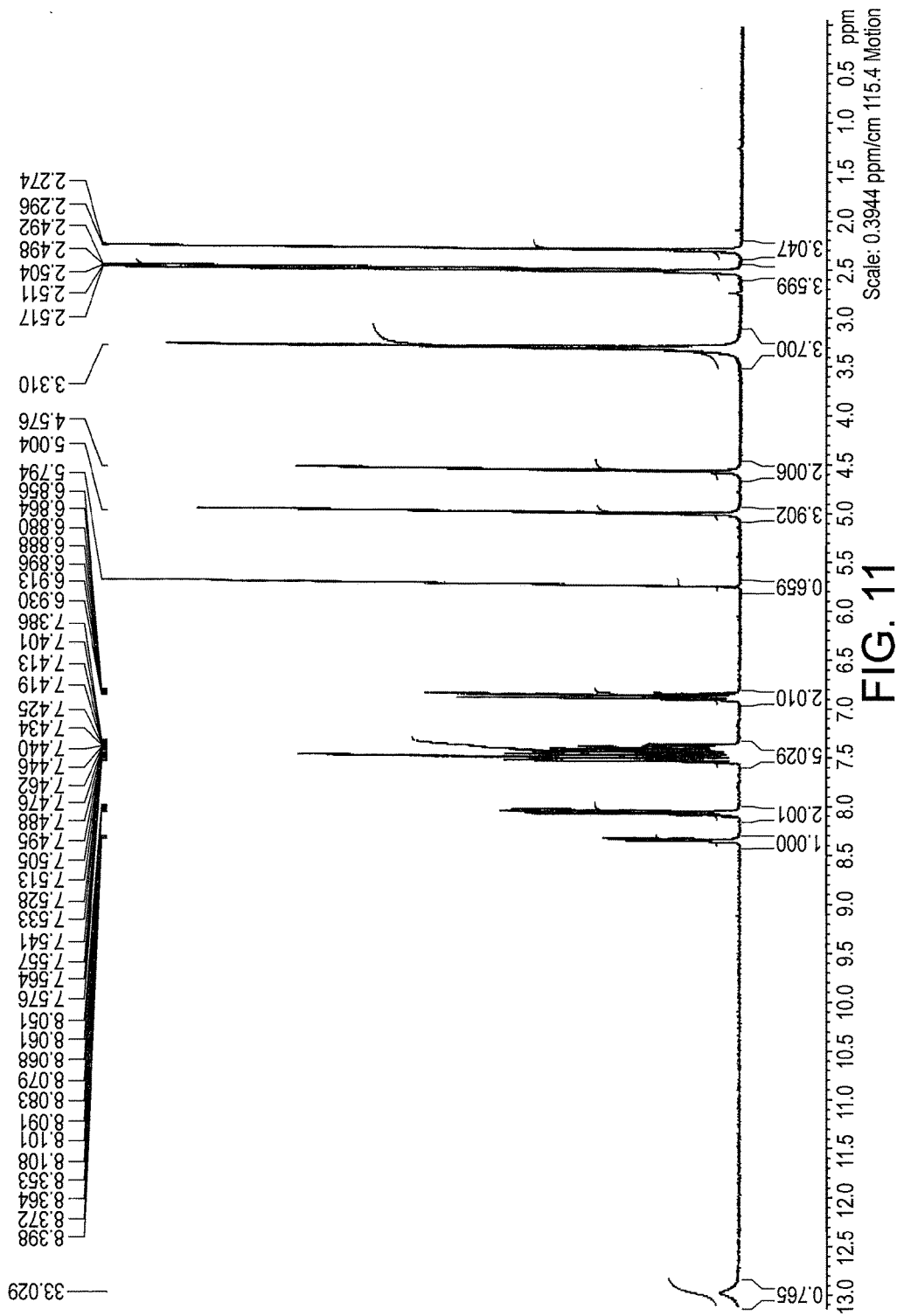

FIG. 11 is a $^1$H NMR plot of the product of Experiment P15 of Example 4 (Polymorphic Form 1) in DMSO-d6.

Figure 12:
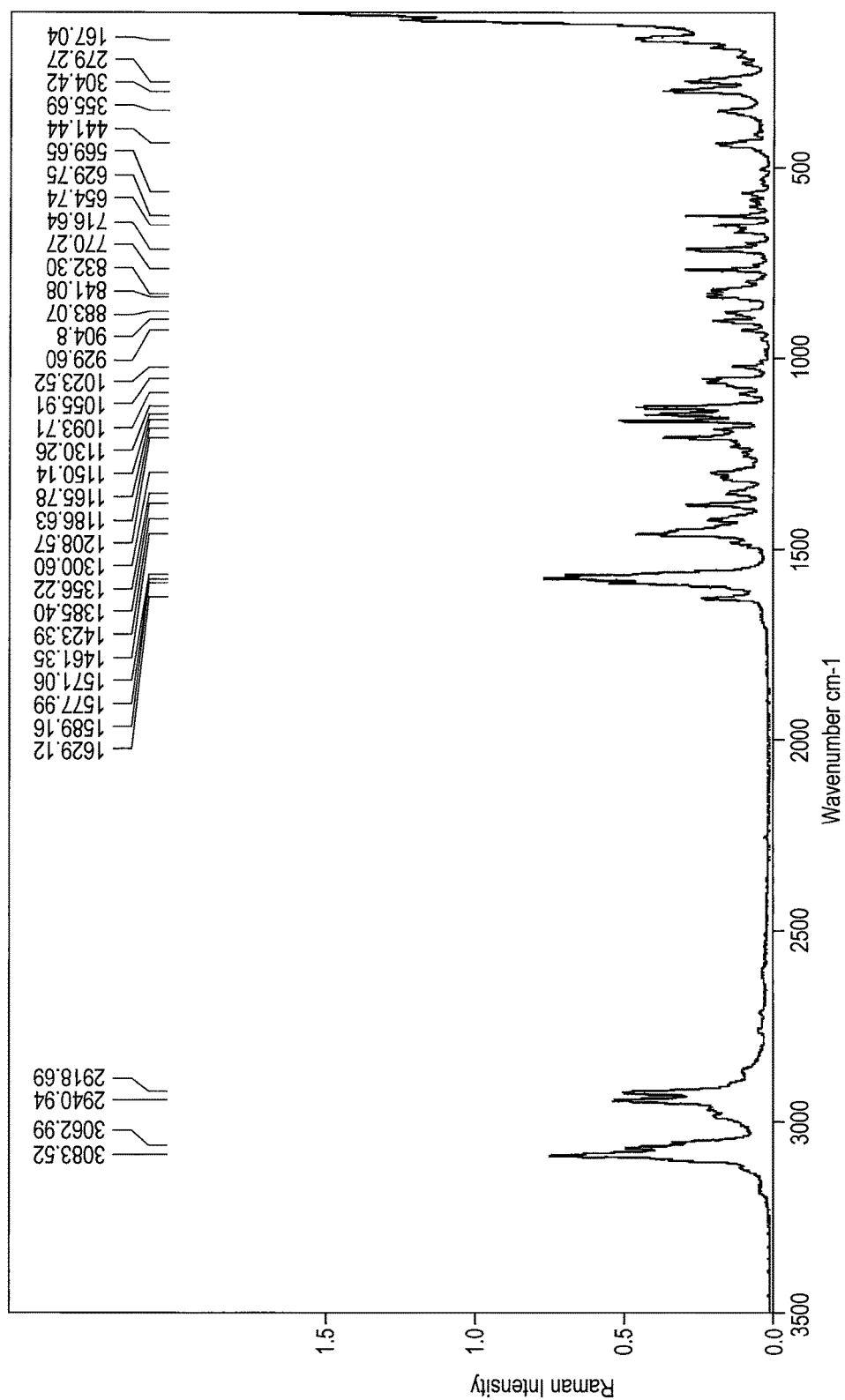

FIG. 12 shows FT-Raman spectrum of the product of Experiment P9 of Example 4 (Polymorphic Form 2).

Figure 13:
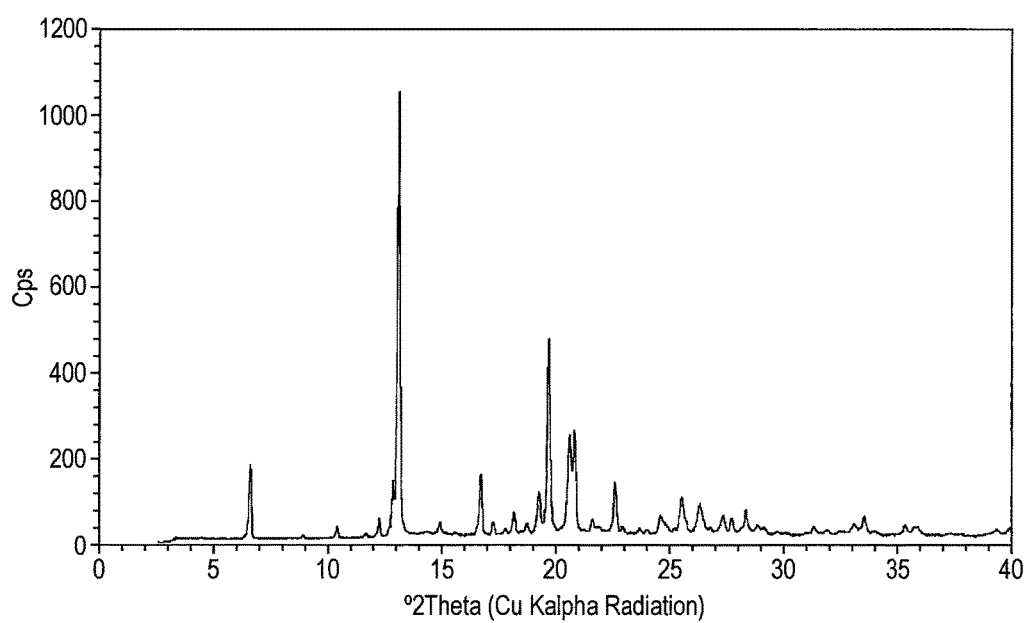

FIG. 13 shows the PXRD pattern of the product of Experiment P9 of Example 4 (Polymorphic Form 2). The material is crystalline.

Figure 14:
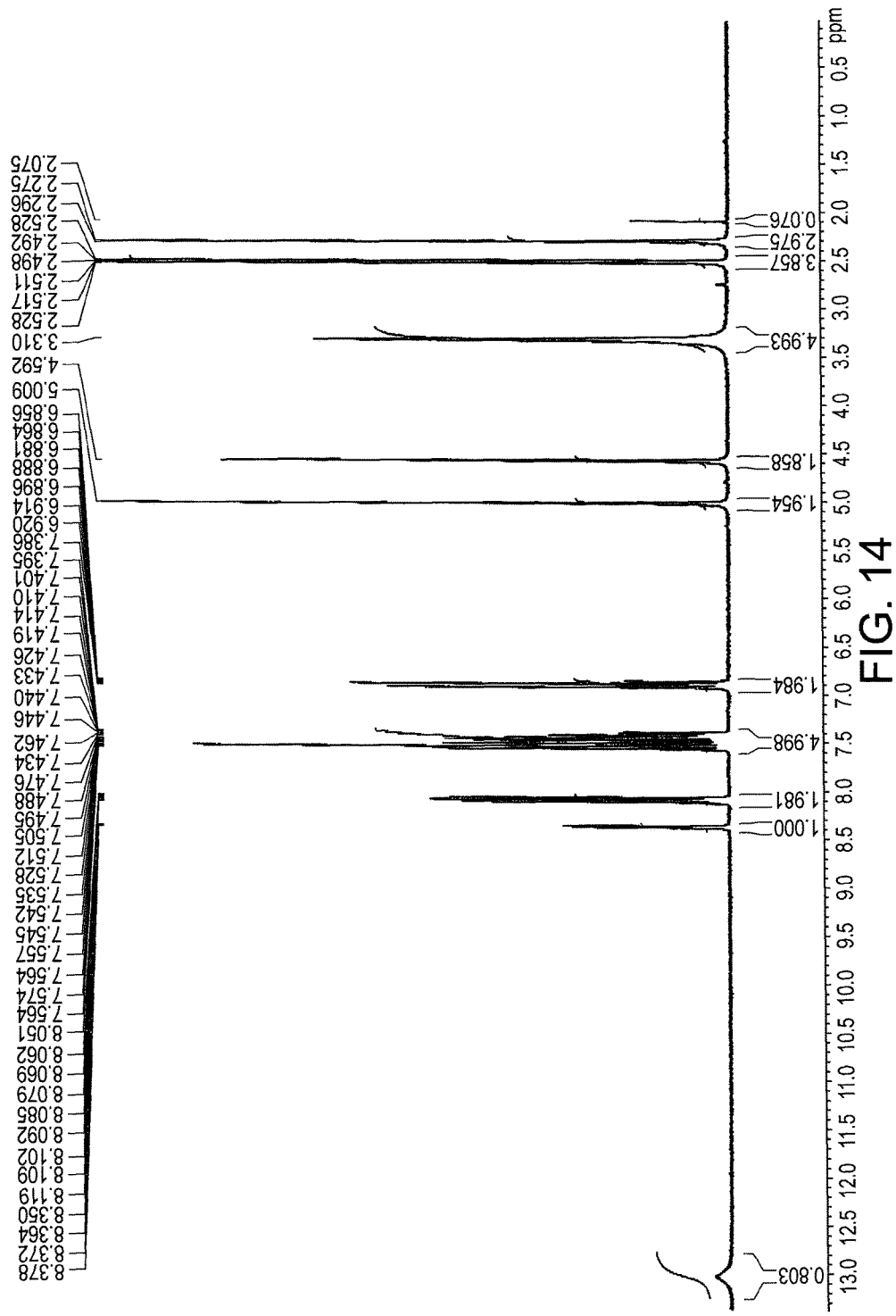

FIG. 14 is a $^1$H NMR was recorded of the product of Experiment P9 of Example 4 (Form 2) in DMSO-d6.

Figure 15:
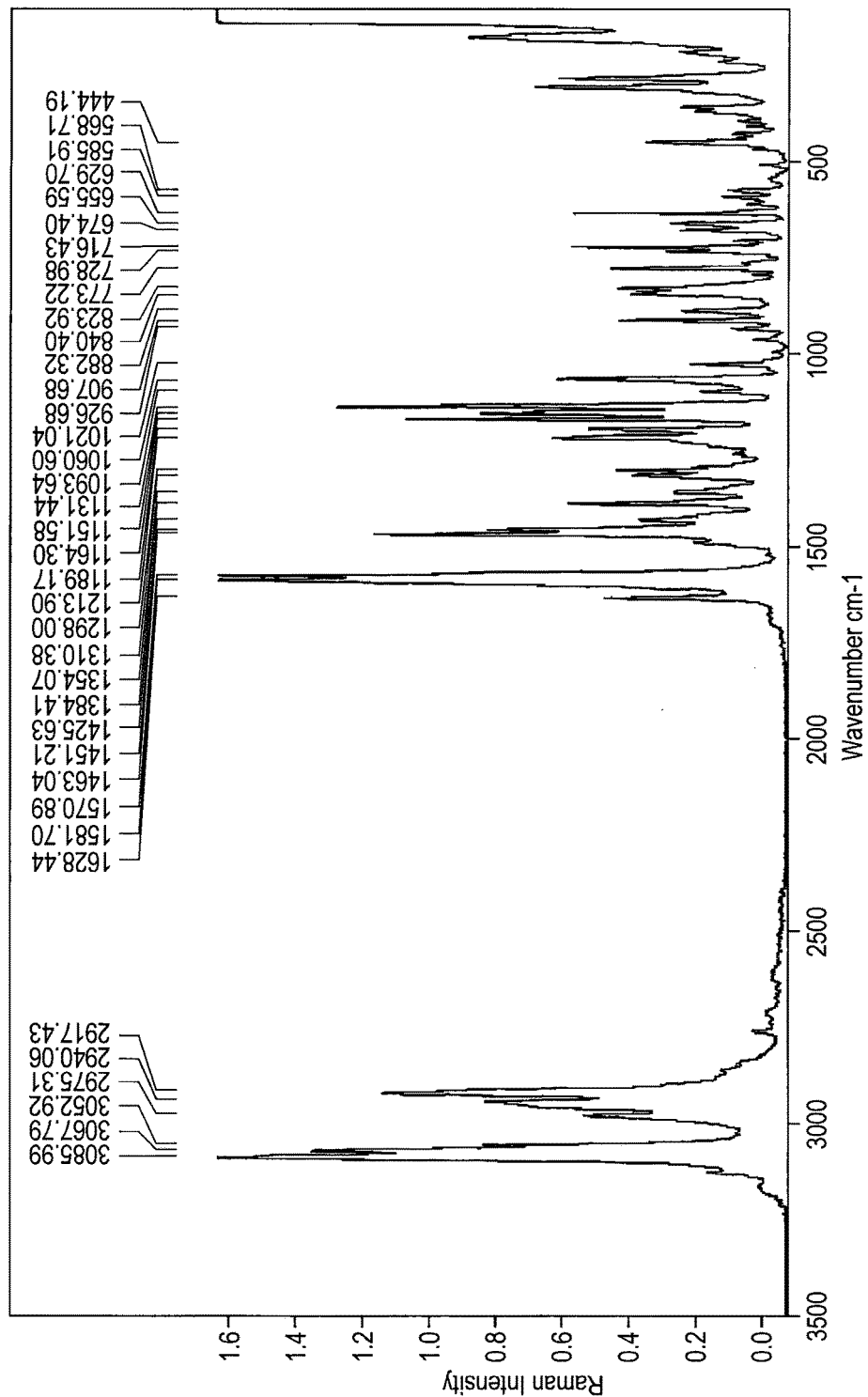

FIG. 15 shows the FT-Raman spectrum of Product P6 of Example 4 (Form 3 in a mixture with Form 2).

Figure 16:
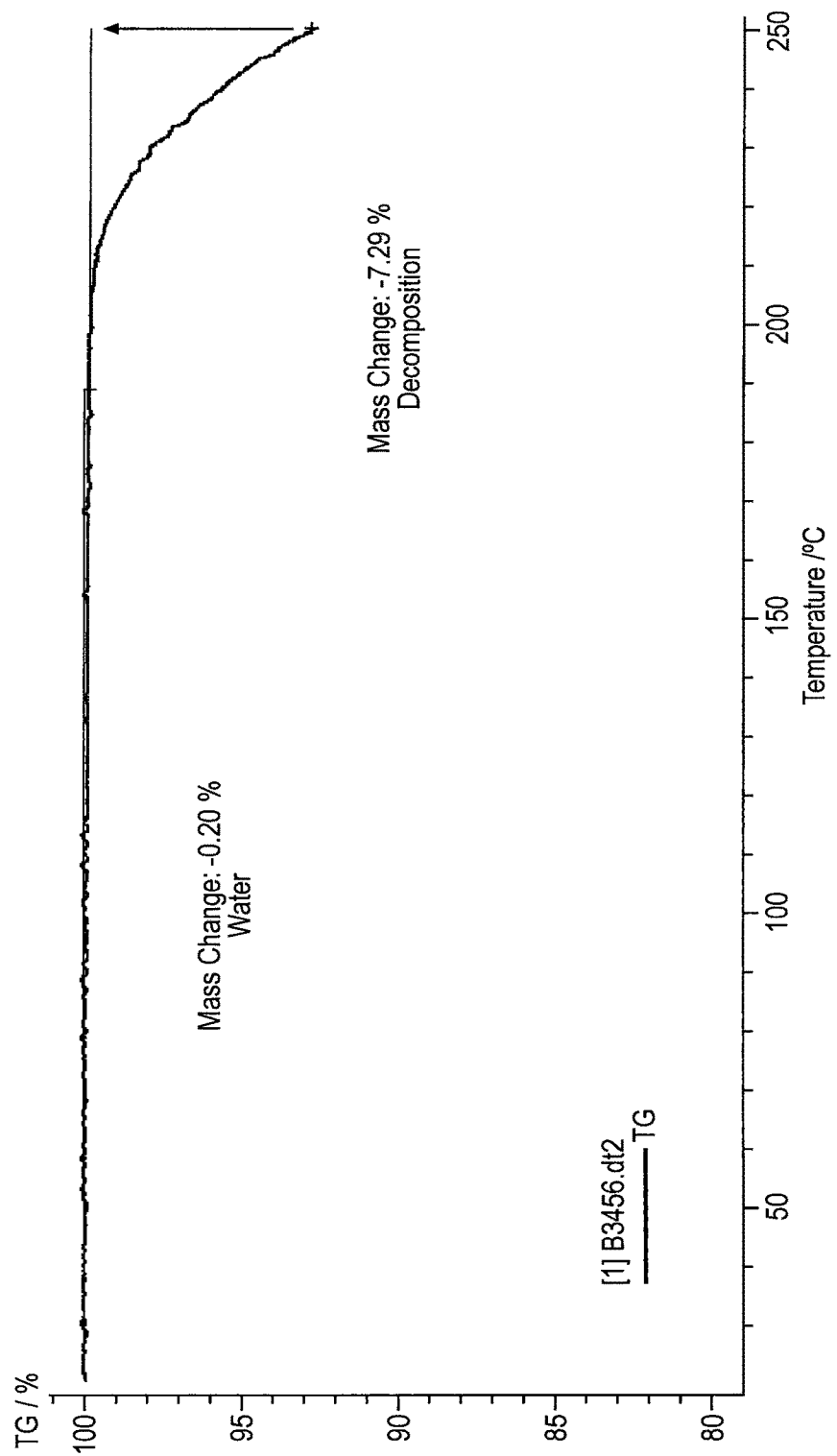

FIG. 16 is a detail of the PXRD pattern of Product P6 of Example 4 in comparison with that of Product P9 of Example 4 (Form 2)

Figure 17:
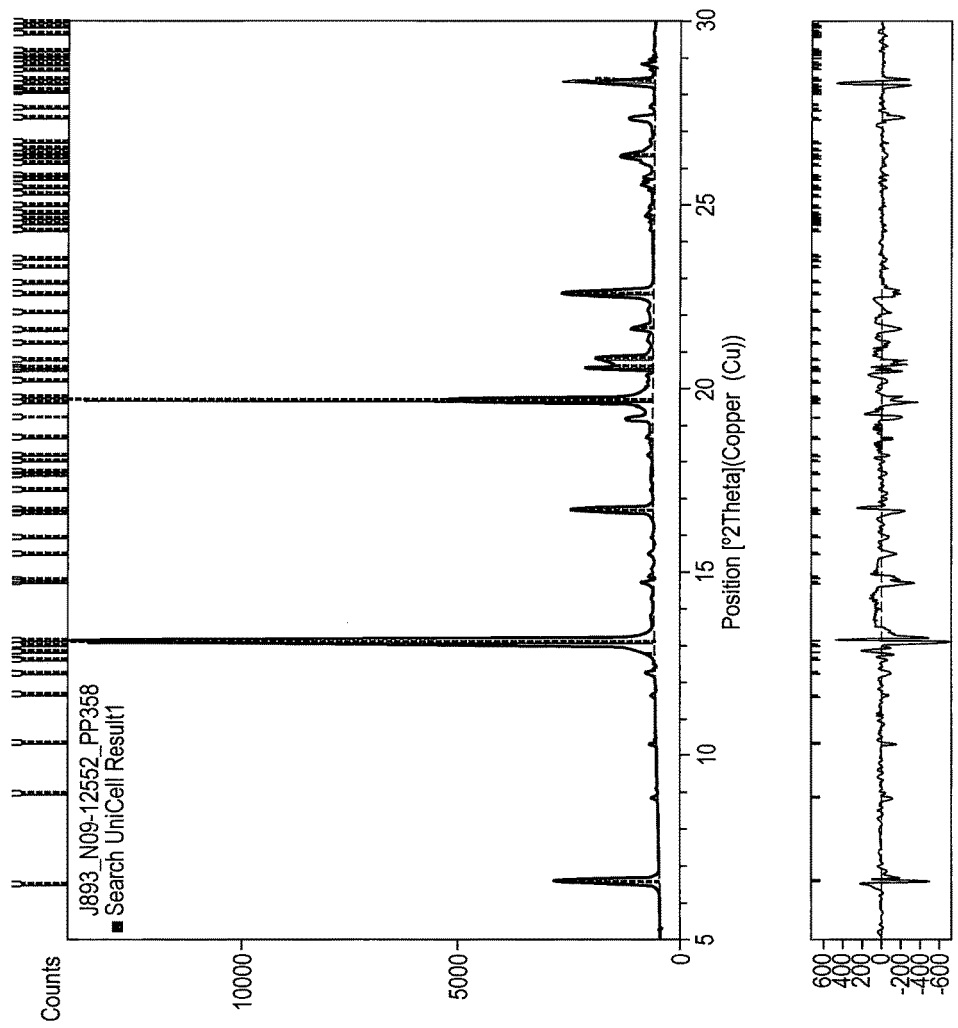

FIG. 17 is a detail of the PXRD pattern of Product P24 of Example 6 (Polymorphic Form 2) showing the fit between the experimental pattern of Product P24 (red, file: J893) and the data calculated based upon a LeBail-fit (blue). Below is the difference plot shown in red.

Figure 18:
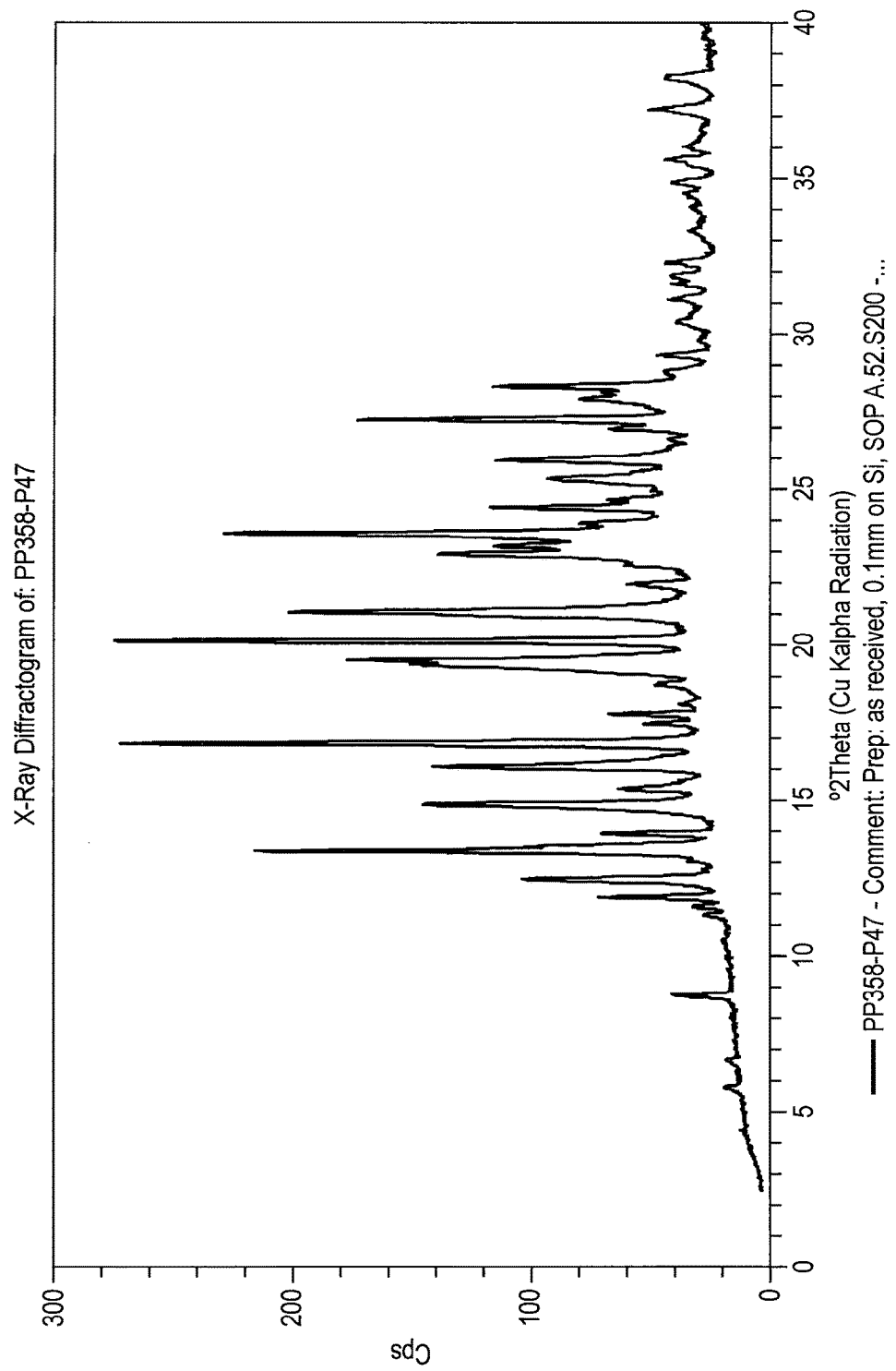

FIG. 18 shows the PRXD pattern of Polymorphic Form 3 (the product of Example 6).

Figure 19:
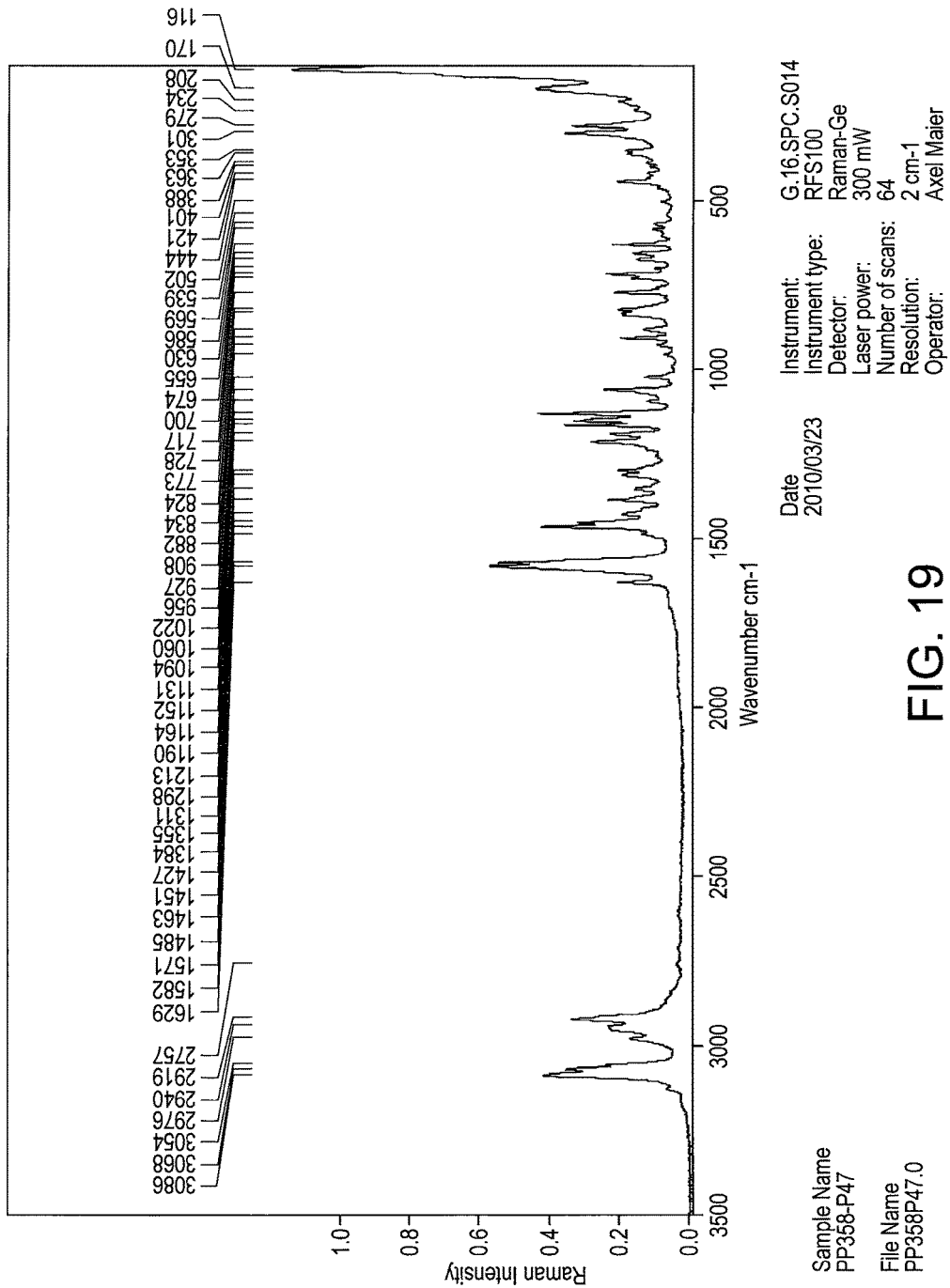

FIG. 19 shows the FT Raman spectrum of Polymorphic Form 3 (the product of Example 6).

In the Examples the following conditions were used for measurements.

1H-NMR: 1H-NMR spectra were recorded using a Bruker DPX300 spectrometer with a proton frequency of 300.13 MHz, a 30° excitation pulse, and a recycle delay of 1 s. 16 scans were accumulated. d6-DMSO was used as the solvent.

DSC: Differential scanning calorimetry was carried out with a Perkin Elmer DSC-7 instrument (closed gold sample pan under $N_2$ atmosphere).

DVS (SPS): Sorption Measurement System SPS11-100n. The sample was placed in an Al crucible, and the sample was allowed to equilibrate at a given r.h. before starting a predefined humidity program. The used measurement program can be recognized in the corresponding figures (blue line).

FT-Raman spectroscopy: FT-Raman spectra were recorded on a Bruker RFS 100 FTRaman system with a near infrared Nd:YAG laser operating at 1064 nm and a liquid nitrogen-cooled germanium detector. For each sample, a minimum of 64 scans with a resolution of 2 cm$^{-1}$ were accumulated. 300 mW laser power was used. The FTRaman data are shown in the region between 3500 to 100 cm$^{-1}$. Below 100 cm-1 the data are meaningless due to the filter cut-off.

Powder X-ray diffraction: Bruker D8; Copper Kα radiation, 40 kV/40 mA; LynxEye detector, 0.02° 2 Theta step size, 37 s step time. Sample preparation: The samples were generally measured without any special treatment other than the application of slight pressure to get a flat surface. Silicon single crystal sample holders were used (0.1 mm deep). The samples were rotated during the measurement.

Solvents: For all experiments, Fluka, Merck or ABCR analytical grade solvents were used.

TG-FTIR: Thermogravimetric measurements were carried out with a Netzsch Thermo-Microbalance TG 209 coupled to a Bruker FTIR Spectrometer Vector 22 or IFS 28 (sample pans with a pinhole, N2 atmosphere, heating rate 10° C./min, range 25° C. up to 250° C.).

In the examples, the following abbreviations are used:
DMSO Dimethylsulfoxide
EtOAc Ethyl acetate
DCM Dichloromethane
TMSOTf Trimethylsilyl triflate
HPLC High performance liquid chromatography
MP Melting Point
LCMS Liquid chromatography mass spectrometry
TLC Thin layer chromatography
THF Tetrahydrofuran
MTBE Methyl $^t$butyl ether
DMF N,N'-dimethylformamide
NMP N-Methyl-2-pyrrolidone
MEK Methylethylketone Example 1—Preparation of [5-fluoro-3-({2-[(4-fluorobenzene)sulfonyl]pyridin-3-yl}methyl)-2-methylindol-1-yl]-acetic acid (Compound 1)

Compound 1 was prepared by the method set out in WO2009/090414 which is as follows.

i. 2-(4-Fluorobenzenesulfonyl)-pyridine-3-carboxaldehyde

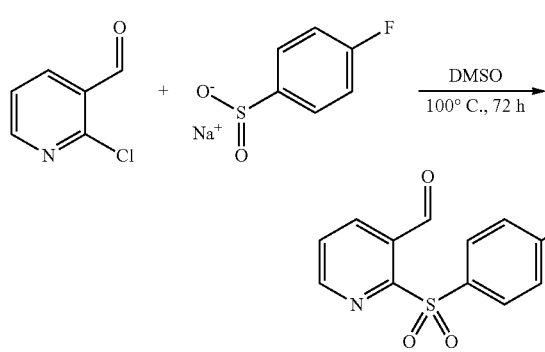

2-Chloro-3-pyridinecarboxaldehyde (4.04 g, 2.86 mmol) and 4-fluorobenzenesulfinic acid sodium salt (5.73 g, 3.14 mmol) were dissolved in DMSO (100 ml) and the mixture was heated at 100° C. for 72 h under nitrogen. Upon cooling to ambient the mixture was diluted with water (500 ml) and extracted with EtOAc (3×). The combined organics were washed with water, brine, dried (MgSO$_4$) and evaporated to dryness to afford 7.89 g of crude product. The crude compound was pre-absorbed onto silica and purified by dry pad suction column chromatography, eluting with heptane using an EtOAc gradient, to afford 4.14 g (41%) of the desired product as a yellow solid (plates) (MP=131-131.3° C.; IR=1691 cm$^{-1}$; HPLC=7.21 min>99%).

$^1$H NMR (400 MHz; CDCl$_3$): 7.23-7.29 (2H, m) 7.60 (1H, dd) 8.05-8.10 (2H, m) 8.37 (2H, dd) 8.67 (1H, dd) 11.1 (1H, s).

$^{13}$C NMR (100 MHz, CDCl$_3$): 116.6 (d) 116.8 (d) 127.3 (d) 130.7 (s) 132.6 (d) 134.0 (s) 137.9 (d) 152.5 (s) 159.7 (s) 165.1 (s) 167.7 (s) 188.5 (d).

ii. [5-Fluoro-3-({2-[4-fluorobenzene)sulfonyl]pyridin-3-yl}methyl)-2-methylindol-1-yl]-acetic acid ethyl ester

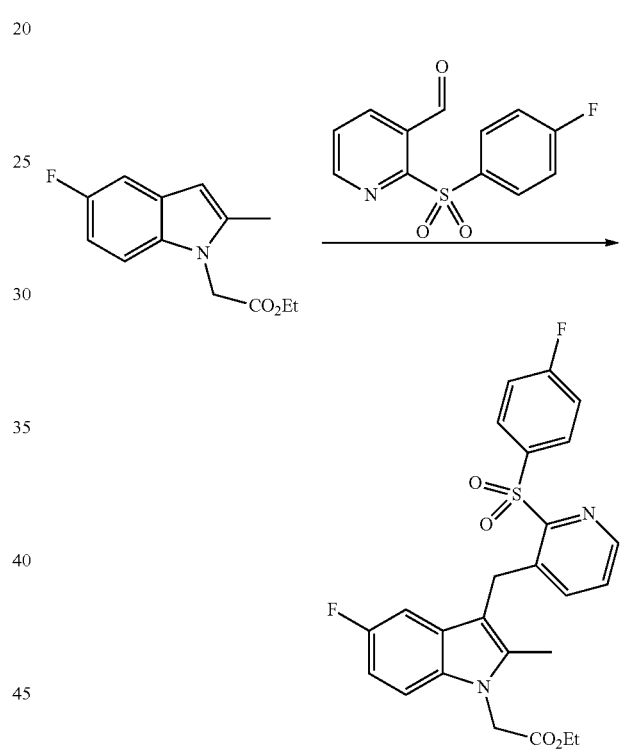

A solution of (5-fluoro-2-methyl-indol-1-yl)-acetic acid ethyl ester (1.0 g, 4.4 mmol) and 2-(4-fluorobenzenesulfonyl)-pyridine-3-carboxaldehyde (1.13 g, 4.3 mmol) in dry DCM (50 ml) was added over 5-10 min to a stirred solution of TMSOTf in dry DCM (15 ml) at 0° C. The mixture was aged for 15 min before the addition of neat triethylsilane (2.05 ml, 12.8 mmol) in one portion. The mixture was stirred for a further 15 h and allowed to warm up to ambient. The reaction was quenched by the drop wise addition of saturated NaHCO$_3$ solution (10 ml) and the biphasic mixture extracted with DCM (2×50 ml). The combined organics were washed with brine (50 ml) then dried (MgSO$_4$) and evaporated to dryness. The reaction was repeated on an identical scale and the two crude materials were purified separately. The crude reaction materials were purified by column chromatography using heptane and an ethyl acetate gradient to afford 0.90 g (43%) and 1.50 g (72%) of the desired compound as a pale purple solid and a brown solid respectively of differing purities (96.0% and 94.5% by HPLC) (MP=150.5-151.5° C., IR=1751 cm⁻¹; HPLC=12.24 min).

¹H NMR (400 MHz; CDCl₃): 1.26 (3H, t) 2.29 (3H, s) 4.22 (2H, q) 4.62 (2H, s) 4.80 (2H, s) 6.79 (1H, dd) 6.86 (1H, ddd) 7.10 (1H, dd) 7.19 (1H, dd) 7.23-7.28 (2H, m) 7.36 (1H, dd) 8.05-8.11 (2H, m) 8.29 (1H, dd).

¹³C NMR (100 MHz, CDCl₃): 10.4 (q) 14.2 (q) 25.3 (t) 45.2 (t) 61.9 (t) 103.4 (d) 103.6 (d) 108.0 (s) 108.1 (s) 109.1 (d) 109.2 (d) 109.5 (d) 109.8 (d) 116.2 (d) 116.4 (d) 127.0 (d) 128.5 (s) 128.6 (s) 132.2 (d) 132.3 (d) 133.3 (s) 135.1 (s) 136.4 (s) 136.6 (s) 139.4 (d) 146.2 (d) 156.2 (s) 157.0 (s) 159.4 (s) 164.7 (s) 167.3 (s) 168.6 (s).

iii. [5-Fluoro-3-({2-[(4-fluorobenzene)sulfonyl]pyridin-3-yl}methyl)-2-methylindol-1-yl]-acetic acid (Compound 1)

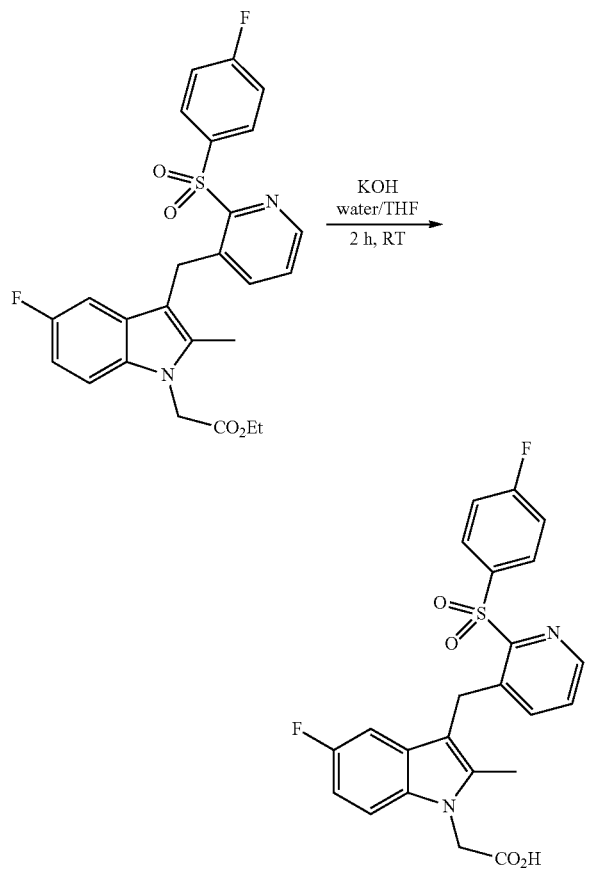 [SMILES: CCOC(=O)Cn1c(C)c(Cc2cccnc2S(=O)(=O)c2ccc(F)cc2)c2cc(F)ccc21 ; Cc1c(Cc2cccnc2S(=O)(=O)c2ccc(F)cc2)c2cc(F)ccc2n1CC(=O)O]

Method A

KOH (0.34 g, 5.94 mmol) was dissolved in water (7 ml) and added to a vigorously stirred solution of [5-fluoro-3-({2-[(4-fluorobenzene)sulfonyl]pyridine-3-yl}methyl)-2-methylindol-1-yl]-acetic acid ethyl ester (0.96 g, 1.98 mmol) in THF (21 ml) under nitrogen at ambient. The reaction was monitored by TLC and LCMS. After 2 h the solvent was removed in vacuo before adjusting the pH to 1.5 using 0.1M HCl solution. The precipitate was stirred vigorously for 15 min before being isolated by suction filtration. The collected solid was washed with water and then MTBE, pulled dry in air and then dried in vacuo at 50° C. to afford 870 mg (97%) of the product as a pink solid (MP=125-126° C.; IR=1729 cm⁻¹; HPLC=10.80 min 99.3%).

¹H NMR (400 MHz; DMSO): 2.29 (3H, s) 4.56 (2H, s) 4.97 (2H, s) 6.85-6.91 (2H, m) 7.37-7.7.45 (2H, m) 7.47 (1H, dd) 7.51-7.57 (2H, m) 8.06-8.15 (2H, m) 8.36 (1H, dd).

¹³C NMR (100 MHz, DMSO): 10.5 (q) 25.0 (t) 45.5 (t) 102.7 (d) 102.9 (d) 107.7 (d) 107.8 (s) 108.8 (d) 109.1 (d) 110.9 (d) 111.0 (d) 117.1 (d) 117.3 (d) 128.1 (d) 128.2 (d) 128.3 (d) 132.7 (d) 132.8 (d) 133.8 (d) 135.5 (s) 136.8 (s) 138.1 (s) 140.4 (d) 147.0 (d) 155.9 (s) 156.6 (s) 158.9 (s) 164.6 (s) 167.1 (s) 171.1 (s).

Batches 1 and 3 of Compound 1 used below were prepared by the method described above, which is identical to the method set out in WO2009/090414. For Batch 2 of Compound 1, the following procedure was used.

Method B

KOH (0.514 g, 9.16 mmol) was dissolved in water (11 ml) and added to a vigorously stirred solution of [5-fluoro-3-({2-[(4-fluorobenzene)sulfonyl]pyridin-3-yl}methyl)-2-methylindol-1-yl]-acetic acid ethyl ester (1.48 g, 3.05 mmol) in THF (32 ml) under nitrogen at ambient. The reaction was monitored by TLC and LCMS. After 2 h, the reaction vessel contained a basic aqueous solution of the potassium salt of compound 1. Instead of removing the solvent as set out in WO2009/090414, the aqueous solution was washed with ethyl acetate to obtain a suspension. The precipitated solid was removed by filtration and the pH of the aqueous phase adjusted to 1.5 using 0.1M HCl solution and stirring vigorously for 15 minutes, before being isolated by suction filtration. The collected solid was washed with water and then MTBE, pulled dry in air and then dried in vacuo at 50° C. to afford 900 mg (64%) of the product as a tan solid.

Example 2—Characterisation of the Product of Example 1

Figure 1:
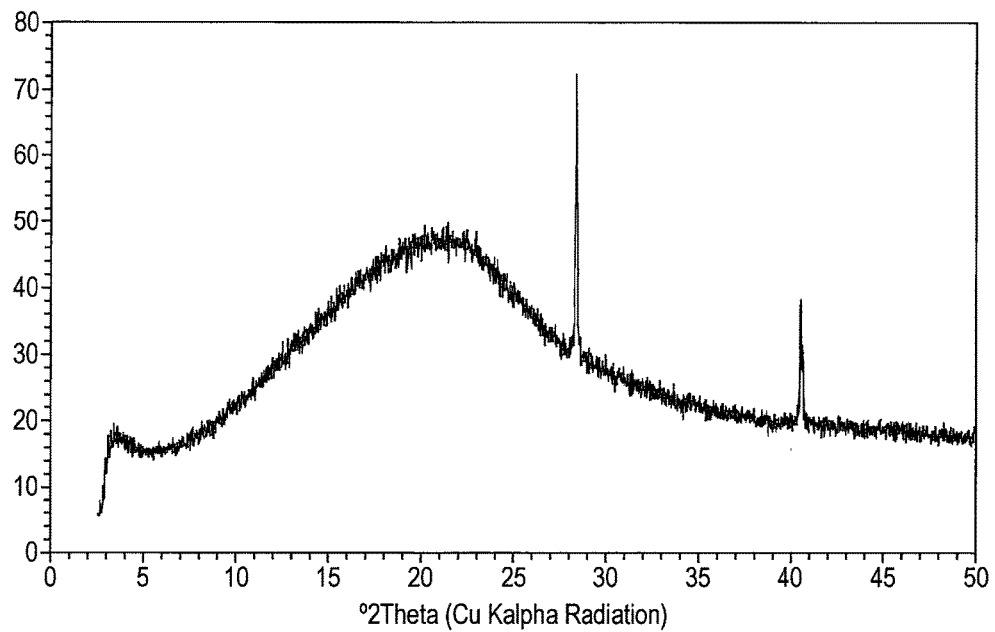
FIG. 1 shows the PXRD pattern of Compound 1, Batch 1.

Three batches of product prepared by the method of Example 1 were characterised by FT-Raman spectroscopy, X-ray powder diffraction (PXRD), Thermogravimetry coupled to Fourier Transform Infrared Spectroscopy (TG-FTIR), differential scanning calorimetry (DSC) and DVS FIG. 1 shows the PXRD pattern of Batch 1. The sample was measured as received. The material is amorphous. The signals at 28.4 °2 Theta and 40.5 °2 Theta could most likely be assigned to KCl.

Figure 2:
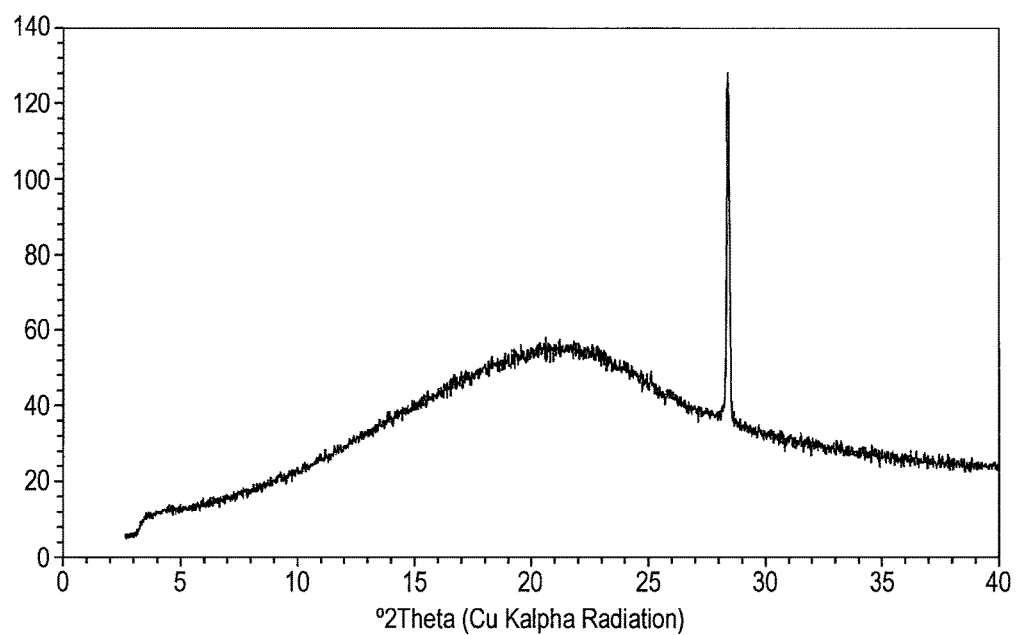
FIG. 2 shows the PXRD pattern of Compound 1, Batch 3.

FIG. 2 shows the PXRD pattern of Batch 3, measured as received. The sample is amorphous. The signal at 28.3 °2 Theta could most likely be assigned to KCl.

FIG. 3 shows the FT-Raman spectrum of Batch 3. The spectrum was used as a reference for the preliminary polymorphism study. The most pronounced Raman peaks are labeled in the figure.

Batch 3 was analyzed by TG-FTIR in a temperature range of 25° C. to 250° C. and a heating rate of 10° C./min. TG-FTIR shows a loss of 1.2 wt.-% mass (residual H₂O) from r.t. to 160° C. Decomposition occurs above ~160° C. Therefore the material is likely a non-solvated form. This is shown in FIG. 4.

Batch 1 was also analyzed by differential scanning calorimetry and FIG. 5 shows the DSC trace. In the first scan (red trace) a glass transition point at about 79° C. (ΔCp: 0.4 J/g*° C.) and a recrystallization signal at about 155° C. is observed. After cooling the sample is still partially amorphous. In the second heating step (blue trace) a glass transition point at about 73° C. with a ΔCp of 0.2 J/g*° C. and a melting signal at about 200° C. with subsequent degradation is observed. The shift of the glass transition point to lower temperatures is probably due to partial decomposition during the first heating step.

In order to examine the behaviour of Batch 1 in the presence of variable water vapour pressure, the sample was analyzed by DVS. The resulting DVS curve with relative humidity over the sample and sample weight percent versus time is shown in FIG. 6. FIG. 7 shows sample weight percent against relative humidity plot. The sample was conditioned at 50% r.h. before starting a pre-defined humidity program with a scanning rate of 5% r.h. change per hour. Below 50% r.h. a continuous mass loss is observed. The sample shows in the second step (0% r.h up to 95% r.h.) a continuous water uptake. At relative humidities above 84% r.h. an increased water uptake is observed. At 95% r.h. no equilibrium is reached. This is typical for amorphous material. At the end of the measurement (end humidity 50% r.h.) the sample has a 0.6% higher mass as the starting material. The sample was checked by FT-Raman (pre- and post DVS measurements). The sample recovered from DVS shows no phase transition.

Similar results were obtained for Batch 3.

Unlike Batches 1 and 3, the PXRD pattern of Batch 2 (FIG. 8) showed that the material was crystalline. The material was prepared using the alternative procedure, Method B, set out above.

Example 3—Recrystallization of Batch 1 of Compound 1

Prior to the salt screening, the KC1 impurity was removed by crystallization of 5 g of Batch 1 of Compound 1 in ethyl acetate. The product was characterized by FT-Raman and TG-FTIR. The TG-FTIR measurement showed a mass loss of 8.2% ethyl acetate at 140° C., which is above the boiling point. This shows that the solvent is strongly bound and is typical for a solvate formation. The sample was dried under vacuum at r.t. and the product was characterized by FT-Raman, TG-FTIR and PXRD. The material changed after drying to a non-solvated form because ethyl acetate was not longer detectable by TG-FTIR. FIG. 9 shows the PXRD pattern of the recrystallised product. The material is crystalline.

The PXRD pattern showed that this recrystallised and dried product was the same crystalline form as Batch 2 of Compound 1 and this crystalline form was designated Form 1.

Example 4—Suspension Equilibration and Cooling Crystallisation Experiments

About 100 mg of Batch 3 was suspended in solvents and solvents mixtures and stirred for 17 days at 22° C. The solids were filtered and analyzed by FT-Raman spectroscopy (2 measurements: 1. wet material, 2. dried material).

An additional suspension equilibration experiment (Exp P23) according to the manufacturing process was performed. To 250 mg of Batch 3, 62.5 µL water and 440 µL formic acid (98%) were added. A yellowish brown suspension was observed. 95 µL toluene was added. After short sonication precipitation was observed. Stirring was not possible. Additionally 1 mL H$_2$O and 80 µL toluene were added. The temperature has being cycled between 25° C. for one hour and 50° C. for two hours (using two hour ramp times) for a total of three days.

For the cooling crystallization experiments, about 100 mg Batch 3 was dissolved at higher temperatures in appropriate amounts of solvent to obtain a saturated solution. To prepare a seed free solution, the temperature was further increased by 5° C. The solutions were subsequently cooled to 5° C. The solids were filtered and analyzed by FT-Raman spectroscopy (2 measurements: 1. wet material, 2. dried material). If no solid was obtained, the solutions were stirred or stored at 5° C. and if still no precipitation was observed, the solutions were evaporated under nitrogen at r.t.

New forms were further characterized by PXRD and TG-FTIR.

Table 1 summarizes the results of the suspension equilibration and cooling crystallization experiments.

TABLE 1

Results of the suspension equilibration and cooling crystallization experiments.

| Exp # | Type 1) | Solvent | T [° C.] | Raman 2) | PXRD 2) | Comments |
|---|---|---|---|---|---|---|
| P2 | SL | Benzyl alcohol | 22 | New | New | probably benzyl alcohol solvate; |
| P3 | SL | DMF/TMBE 1:5 | 22 | New | New | probably DMF solvate; TG-FTIR shows a loss of DMF along with the decomposition. |
| P4 | SL | DMSO | 22 | New | New | DMSO solvate; TG-FTIR shows a loss of DMSO along with the decomposition |
| P5 | SL | DMSO/ toluene 1:19 | 22 | P4 | — | Same as Exp. P4 |
| P6 | SL | Methylethylketone | 22 | New | New | non-solvated form Form 2 + Form 3 |
| P7 | SL | THF | 22 | New | 3) | TG-FTIR shows a loss of 12.4% of THF at ≥100° C.; (theoretical content for mono solvate: 13.6%); after drying the FT Raman agrees with that of Batch 2 and the recrystallised product |

TABLE 1-continued

Results of the suspension equilibration and cooling crystallization experiments.

| Exp # | Type 1) | Solvent | T [° C.] | Raman 2) | PXRD 2) | Comments |
|---|---|---|---|---|---|---|
| | | | | | | of Example 3, i.e. Form 1 |
| P8 | SL | NMP/cyclohexane 1:1 | 22 | New | New | Solvate |
| P9 | SL | water/acetonitrile 1:1 (aw: ~0.92) | 22 | New | New | Non-solvated form: Form 2 |
| P10 | SL | water/THF 1:1 (aw: ~1) | 22 | New | New | TG-FTIR shows a loss of 42.5% of water; most likely hydrate + surface bound water |
| P11 | SL | methanol | 22 | New | New | TG-FTIR shows a loss of 6.4% of MeOH ≥110° C.; (theoretical content for mono solvate: 6.6%) |
| P12 | SL | Acetonitrile | 22 | P9 | — | Agrees with Exp P9, i.e. Form 2 |
| P13 | SL | Acetone | 22 | New | 3) | TG-FTIR shows a loss of 7.7% of acetone ≥110° C.; (theoretical content for hemi solvate: 6.0%); after drying the FT Raman agrees with that of Batch 2 and the recrystallised product of Example 3, i.e. Form 1 |
| P14 | SL | Formic acid | 22 | New | 3) | TG-FTIR shows a loss of 8.2% of formic acid; most likely solvate + surface bound solvent; after drying the FT Raman agrees with that of Batch 2 and the recrystallised product of Example 3, i.e. Form 1 |
| P15 | SL | Dichloromethane | 22 | Form 1 | — | FT Raman agrees with that of Batch 2 and the recrystallised product of Example 3, i.e. Form 1 |
| P16 | SL | 2-propanol | 22 | New | New | TG-FTIR shows a loss of 11.9% of 2-PrOH ≥110° C.; (theoretical content for mono solvate: 11.6%) |
| P17 | COL/evap | water/acetone 1:1 (aw: ~0.9) | 55-5 | New | New | TG-FTIR shows a loss of 22.0% of water; most likely hydrate + surface bound water |
| P18 | COL/evap | TBME/Dioxane 1:3 | 55-5 | — | — | gel |
| P20 | COL | Ethanol | 75-5 | New | 3) | TG-FTIR shows a loss of 27.7% of ethanol; most likely solvate + surface bound solvent; after drying the FT Raman agrees with that of Batch 2 and the recrystallised product of Example 3, i.e. Form 1 |
| P21 | COL | DMSO/toluene 1:9 | 80-5 | P4 | | similar to Experiment P4, slight differences in PXRD |

TABLE 1-continued

Results of the suspension equilibration and cooling crystallization experiments.

| Exp # | Type 1) | Solvent | T [° C.] | Raman 2) | PXRD 2) | Comments |
|---|---|---|---|---|---|---|
| P22 | COL/evap | Formic acid | 80-5 | New | — | degradation |
| P23 | SL | water/formic acid/toluene | 25-50 | New | New | TG-FTIR shows a loss of 9.4% of toluene with a trace of water ≥150° C.; (theoretical content for hemi solvate: 9.2%) |

1) Type: SL = suspension equilibration experiment; COL: cooling crystallization experiment.
2) new: spectrum/pattern different from starting material is observed which is the same as that of Form 1 (Batch 2 and the recrystallised product of Example 3).
3) The PXRD are similar to Compound 1, Batch 2. The recovered material from PXRD was measured by FT Raman. The spectra agree with the spectrum of Compound 1, Batch 2 and the recrystallised product of Example 3.

In summary:

Experiments P2, P3, P4, P5, P8, P10, P11, P16, P17, P21 and P23 led to the formation of solvates (including hydrates) or hemisolvates;

Experiment P18 gave rise to a gel product;

Experiment P22 led to a product which degraded;

Experiments P7, P13, P14, P15 and P20 gave rise to crystalline Form 1 (i.e. the same polymorphic form as Batch 2 of Compound 1 and the product of Example 3);

Experiments P9 and P12 gave rise to a new crystalline form, designated Form 2; and Experiment P6 led to the formation of polymorphic Form 2 in admixture with a third polymorphic form, designated Form 3.

Example 5—Further Characterisation of Polymorphic Forms i. Polymorphic Form 1

As detailed above, the recrystallisation experiment of Example 3 gave rise to a product which was probably an ethyl acetate solvate. On drying, however, it changed to a non-solvated form, designated Form 1. After drying, the products of Experiments P7 (THF solvate), P13 (acetone solvate), P14 (formic acid solvate), P15 (dichloromethane solvate) and P20 (ethanol solvate) adopted a crystalline form which appeared from the Raman spectrum to have the same characteristics as Batch 2 of Compound 1 and of the recrystallised product of Example 3. Due to instability, it was not possible to determine the stoichiometry of the solvates.

This polymorphic form was designated Form 1 and it was further characterised by PXRD. Indexing of PXRD can be used to determine if a given pattern corresponds to a pure solid phase. The PXRD pattern of the recrystallised material (file: H906) could be successfully indexed, and the lattice was found to be triclinic. The resulting lattice parameters can be seen in Table 2. The final fit between the observed and calculated diffraction patterns is shown in FIG. 10 and the low R-values (see Table 2) confirm the good fit. This confirms that Form 1 corresponds to a true polymorphic form and not to a mixture of forms.

TABLE 2

Lattice parameters and LeBail-Fit details for the laboratory PXRD data for Form 1 obtained at room temperature.

| file | H906 |
|---|---|
| a | 10.6 ± 0.1 Å |
| b | 12.8 ± 0.1 Å |
| c | 9.1 ± 0.1 Å |
| α | 102 ± 1° |
| β | 112 ± 1° |
| γ | 89 ± 1° |
| cell volume | 1.116 Å$^3$ |
| $R_P$ | 3.8% |
| weighted $R_P$ | 6.7% |

A $^1$H NMR was recorded of the product of Experiment P15 (Polymorphic Form 1) in DMSO-d6. The spectrum confirms Chemical integrity (see FIG. 11).

ii. Polymorphic Form 2

Form 2 was obtained by phase equilibration experiments at room temperature. in water/acetonitrile (1:1) (Experiment P9) and acetonitrile (Experiment P12). The phase equilibration experiment at r.t. in ethyl methyl ketone (Experiment P6) also gave rise to Form 2 in a mixture with another new form (Form 3).

The FT-Raman Spectrum of the product of Experiment P9 of Example 4 (Form 2) is shown in FIG. 12 and its PXRD pattern is shown in FIG. 13. It could successfully be indexed and this confirms that Form 2 corresponds to a true polymorphic form and not to a mixture of forms.

A $^1$H NMR was recorded of the product of Experiment P9 of Example 4 (Form 2) in DMSO-d6 (see FIG. 14). The spectrum confirms chemical integrity.

iii. Polymorphic Form 3

Form 3 was obtained as a mixture with form 2 by a phase equilibration experiment at r.t. in ethyl methyl ketone (Example 4, Experiment P6). FIG. 15 shows the FT-Raman spectrum of Product P6 (Form 3 in a mixture with Form 2). The most pronounced Raman peaks are labelled in the figure.

PXRD of Product P6 showed that the material was crystalline and FIG. 16 shows the PXRD pattern of Product P6 in comparison to that of Product P9 (Form 2).

Product P6 shows all signals of Product P9 and also additional signals. This indicates that Product P6 is a mixture of Form 2 and another form. This other form was designated Form 3.

Example 6—Preparation of Pure Polymorphic Form 3

A. 20.8 mg of Compound 1, mixture of Forms 2 and 3 (similar to that obtained by the method of Example 4, P6)

and 21.4 mg of Compound 1, Form 2 (similar to that obtained by the method of Example 4, P9) was suspended in 0.2 mL of MEK and the mixture heated up to 70° C. When the Compound 1 was nearly completely dissolved, a further 9.8 mg of Compound 1, Form 2+Form 3 (similar to that obtained by Example 4, P6) and 10.3 mg of Compound 1, Form 1 (similar to that of Example 4, P9) was added. The solvent was partially evaporated under nitrogen flow, a further 0.1 mL of MEK added and the mixture stirred for 25-26 h at 75° to obtain a yellowish brown suspension. The solid was recovered by filter centrifugation (5000 rpm, 0.2 μm PTFE, 22° C.) and the material analyzed by PXRD and shown to be Compound 1, polymorphic Form 3.

B. In order to obtain a purer Form 3 product, the crystals obtained from A above were used to seed a saturated solution prepared as follows. 286.0 mg of Compound 1, Form 1 was suspended in 0.2 mL of MEK. The mixture was sonicated for ~1 min and precipitation was observed. Following this, an additional 0.1 mL of MEK was added, the solution was heated up to 75° C. and seeded with ~1 mg of the crystals obtained from A above. The solution was stirred for ~22 h at 75° C. and a solid recovered by filter centrifugation (0.2 μm PTFE, 1 min, 15000 rpm, 25° C.); vessel flushed with 0.05 mL of MEK. The material was dried for ~24 h under vacuum at r.t. and the solid product analyzed by FT Raman and PXRD and shown to be Compound 1, Form 3.

C. In order to obtain a still purer Form 3 product, 149.7 mg of Compound 1, Polymorphic Form 1 was suspended in 0.15 mL of MEK. The mixture was sonicated for ~1 min, following which precipitation was observed. An additional 0.075 mL of MEK was added and the mixture heated up to 75° C. The solvent was partially evaporated under nitrogen flow evaporated; 0.05 mL of MEK added and the mixture seeded with ~2 mg of crystals obtained in B above. The solution was then stirred for ~8 h at 75° C. and a solid recovered by filter centrifugation (0.2 μm PTFE, 1 min, 15000 rpm). The material was dried overnight under vacuum at r.t. and the solid product analyzed by PXRD (FIG. 18) FT Raman (FIG. 19) and shown to be Polymorphic Form 3 of Compound 1.

Example 7—Thermodynamic Stability of Polymorphic Forms

A mixture with similar ratios of the products of Example 4, Experiment 15 (Form 1), Example 4, Experiment 9 (form 2+x) and Example 4, Experiment 6 (Form 2+Form 3) were suspended in acetonitrile and shaken for 13 days at 22° C. to give a product designated Product P24). The solid was recovered by filter centrifugation and characterized by PXRD. FIG. 16 shows the PXRD pattern of Product P24 compared with that of the product of Experiment P9 of Example 4. The two PXRD patterns are essentially the same although that of Product P9 shows a few additional signals. These signals could be assigned to (i) another crystalline form or (ii) the signals could not be detected for Product P24 because the diffractogram has a lower intensity.

Thus, after 13 days at 22° C. the PXRD corresponds to that of Form 2. Based on this result it can be deduced that Form 2 is the most stable form at room temperature.

Indexing of PXRD can be used to determine if a given pattern corresponds to a pure solid phase. The PXRD pattern of Product P24 (file: J893) could be successfully indexed, and the lattice was found to be triclinic. The resulting lattice parameters can be seen in Table 3. The final fit between the observed and calculated diffraction patterns is shown in FIG. 17 and the low R-values (see Table 3) confirm the good fit.

This confirms that Form 2 corresponds to a true polymorphic form and not to a mixture of forms.

Product P9 of Example 4 could also be indexed within the same space group and similar lattice parameters. However, some few signals of product P9 could not be indexed. These signals could be assigned to another crystalline form (maybe e.g. polymorph, impurity or degradation).

TABLE 3

Lattice parameters and LeBail-Fit details for the laboratory PXRD data for Form 2 obtained at room temperature.

| Sample | Product P24 |
|---|---|
| file | J893 |
| a | 10.8 ± 0.1 Å |
| b | 13.9 ± 0.1 Å |
| c | 7.8 ± 0.1 Å |
| α | 101. ± 1° |
| β | 110 ± 1° |
| γ | 79 ± 1° |
| cell volume | 1.068 Å$^3$ |
| RP | 4.9% |
| Weighted RP | 7.1% |

Example 8—Solubility of Polymorphic Forms

The solubility of Form 1, Form 2 and Form 3 was determined by HPLC in fasted state simulated intestinal fluid (FaSSIF) and fed state simulated intestinal fluid (FeSSIF) at 25° C. FaSSIF and FeSSIF were prepared from SIF powder, available at PHARES, Switzerland. Suspensions of both forms were prepared and equilibrated for 24 hours at 25° C. The suspensions were filtered. The pH values of the resulting saturated solutions were measured. The filtrates were diluted and analyzed by HPLC using a general, unoptimized method. The values listed below are averages over multiple repetitions. Additionally Raman spectra of the recovered solids were recorded.

TABLE 4

| Crystalline Form | Solvent | Solubility (mg/mL) | FT Raman | pH of Saturated solution |
|---|---|---|---|---|
| Form 2 | FeSSIF | 0.35 | Agrees with Form 2 | 5.0 |
| Form 1 | FeSSIF | 1.18 | Differences from Form 1 | 4.9 |
| Form 3 | FeSSIF | 2.12 | Agrees with Form 3 | 5.0 |
| Form 2 | FaSSIF | 0.55 | Agrees with Form 2 | 6.1 |
| Form 1 | FaSSIF | 0.72 | Agrees with Form 1 | 5.7 |
| Form 3 | FaSSIF | 1.31 | Agrees with Form 3 | 5.4 |

The results set out in Table 4 show that Form 3 is more soluble in both FaSSIF and FeSSIF. This increased solubility will make formulation of Form 3 easier and it is possible that it may also to lead to increased bioavailability for oral formulations of the compound.

The invention claimed is:

1. A polymorphic form of [5-fluoro-3-({2-[(4-fluorobenzene)sulfonyl]pyridin-3-yl}methyl)-2-methylindol-1-yl]-acetic acid (Compound 1), characterised in that it gives an FT-Raman spectrum which is characterised by peaks at 3068±2 cm$^{-1}$, 3054±2 cm$^{-1}$, 2976±2 cm$^{-1}$, 1582±2 cm$^{-1}$, 1427±2 cm$^{-1}$, 1298±2 cm$^{-1}$, 1213±2 cm$^{-1}$, 1190±2 cm$^{-1}$, 1164±2 cm$^{-1}$, 1060±2 cm$^{-1}$, 956±2 cm$^{-1}$, 927±2 cm$^{-1}$, 834±2 cm$^{-1}$, 700±2 cm$^{-1}$, 502±2 cm$^{-1}$, 421±2 cm$^{-1}$, 401±2 cm$^{-1}$, 388±2 cm$^{-1}$, 363±2 cm$^{-1}$, 353±2 cm$^{-1}$, 301±2 cm$^{-1}$, 208±2 cm$^{-1}$, 116±2 cm$^{-1}$.

2. The polymorphic form of Compound 1 of claim 1 which comprises not more than 2% of other forms of Compound 1.

3. The polymorphic form of Compound 1 of claim 1 which comprises not more than 0.1% by weight of solvent.

4. A process for the preparation of the polymorphic form of Compound 1 of claim 1 comprising:
   (a). suspending [5-fluoro-3-({2-[(4-fluorobenzene)sulfonyl] pyridin-3-yl}methyl)-2-methylindol-1-yl]-acetic acid in methylethylketone;
   (b). stirring the suspension at a temperature of about 15 to 25° C. for 15 to 30 days; and
   (c). isolating and drying the solid [5-fluoro-3-({2-[(4-fluorobenzene)sulfonyl]pyridin-3-yl}methyl)-2-methylindol-1-yl]-acetic acid.

5. The process of claim 4, further comprising:
   (d). dissolving the product of (c) in methyl ethyl ketone at an elevated temperature of from about 65 to 80° C. to obtain a saturated solution;
   (e). partially evaporating the solvent;
   (f). stirring the mixture for 20-36 hours such that crystallisation takes place; and
   (g). isolating the crystalline Compound 1.

6. The process of claim 5, further comprising:
   (h). preparing a saturated solution of Compound 1 in methylethylketone at an elevated temperature of about 65-80° C.;
   (i). seeding the solution with the crystalline product of (g);
   (j). allowing crystallisation to take place; and
   (k). isolating the crystalline product.

7. The process of claim 6 comprising repeating (h) to (k) using the product of (k) as the seed crystals for (i).

8. A method for the treatment of a CRTH2-mediated disease or condition selected from the group consisting of asthma, asthma exacerbations, chronic obstructive pulmonary disease, allergic rhinitis conjunctivitis, nasal polyps, atopic dermatitis, contact hypersensitivity (including contact dermatitis), eosinophilic cough, eosinophilic bronchitis, eosinophilic gastroenteritis, eosinophilic esophagitis, food allergies, inflammatory bowel disease, ulcerative colitis, Crohn's disease, mastocytosis, urticaria, hypereosinophilic syndrome, hyper IgE syndrome, fibrotic diseases, Churg-Strauss syndrome, and multiple sclerosis, comprising administering to a patient in need of such treatment an effective amount of the polymorphic form of Compound 1 of claim 1.

9. A method for the treatment of asthma exacerbations induced by respiratory syncytial virus or rhinovirus, comprising administering to a patient in need of such treatment an effective amount of the polymorphic form of Compound 1 of claim 1.

10. A pharmaceutical or veterinary composition comprising the polymorphic form of Compound 1 of claim 1 and a pharmaceutically or veterinarily acceptable excipient.

11. The composition of claim 10 further comprising one or more additional active agents useful in the treatment of diseases and conditions mediated by $PGD_2$ or other agonists at the CRTH2 receptor.

12. The composition of claim 11 wherein the additional active agent is selected from:
   other CRTH2 receptor antagonists;
   Suplatast tosylate and similar compounds;
   β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol or methylxanthines such as theophylline and aminophylline, mast cell stabilisers such as sodium cromoglycate or muscarinic receptor antagonists such as tiotropium;
   antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;
   $\alpha_1$ and $\alpha_2$ adrenoreceptor agonists such as propylhexedrine phenylephrine, phenylpropanolamine, pseudoephedrine, naphazoline hydrochloride, oxymetazoline hydrochloride, tetrahydrozoline hydrochloride, xylometazoline hydrochloride and ethylnorepinephrine hydrochloride;
   modulators of chemokine receptor function, for example CCR1, CCR2, CCR2A, CCR2B, CCR3, CCR4, CCR5, CCR6, CCR7, CCR8, CCR9, CCR10 and CCR11 (for the C—C family) or CXCR1, CXCR2, CXCR3, CXCR4 and CXCR5 (for the C—X—C family) and $CX_3CR1$ for the C—$X_3$—C family;
   Leukotriene antagonists such as montelukast, pranlukast and zafirlukast
   leukotriene biosynthesis inhibitors such as 5-lipoxygenase inhibitors or 5-lipoxygenase activating protein (FLAP) inhibitors such as zileuton, ABT-761, fenleuton, tepoxalin, Abbott-79175, N-(5-substituted)-thiophene-2-alkylsolfonamides, 2,6-di-tert-butylphenol hydrazones, methoxytetrahydropyrans such as ZD2138, SB-210661, pyridinyl-substituted-2-cyanonaphthalene compounds such as L-739010, 2-cyanoquinoline compounds such as L-746,530, indole and quinoline compounds such as MK-591, MK-886 and BAY x 1005;
   Phosphdiesterase inhibitors, including PDE4 inhibitors such as roflumilast;
   anti-IgE antibody therapies such as omalizumab;
   anti-infectives such as fusidic acid (particularly for the treatment of atopic dermatitis);
   anti-fungals such as clotrimazole (particularly for the treatment of atopic dermatitis);
   immunosuppressants such as tacrolimus and particularly pimecrolimus in the case of inflammatory skin disease or alternatively FK-506, rapamycin, cyclosporine, azathioprine or methotrexate;
   Immunotherapy agents including allergen immunotherapy such as Grazax;
   corticosteroids such as prednisone, prednisolone, flunisolide, triamcinolone acetonide, beclomethasone dipropionate, budesonide, fluticasone propionate mometasone furoate and fluticasone furoate drugs which promote Th1 cytokine response such as interferons, TNF or GM-CSF;
   other antagonists of $PGD_2$ acting at other receptors such as DP antagonists;
   drugs that modulate cytokine production such as inhibitors of TNFα converting enzyme (TACE) anti-TNF monoclonal antibodies, TNF receptor immunoglobulin molecules, inhibitors of other TNF isoforms, non-selective COX-1/COX-2 inhibitors such as piroxicam, diclofenac, propionic acids such as naproxen, flubiprofen, fenoprofen, ketoprofen and ibuprofen, fenamates such as mefanamic acid, indomethacin, sulindac and apazone, pyrazolones such as phenylbutazone, salicilates such as aspirin; COX-2 inhibitors such as meloxicam, celecoxib, fofecoxib, valdecoxib and etoricoxib, low dose methotrexate, lefunomide, ciclesonide, hydroxychloroquine, d-penicillamine, auranofin or parenteral or oral gold;

drugs that modulate the activity of Th2 cytokines IL-4 and IL-5 such as blocking monoclonal antibodies and soluble receptors for Th2 cytokines;

PPAR-γ agonists such as rosiglitazone; or with anti-RSV antibodies such as Synagis (palivizumab) and agents that may be used to treat rhinovirus infection in the future e.g. interferon-alpha, interferon-beta or other interferons.

13. A kit for the treatment of a disease or condition mediated by the action of PGD2 at the CRTH2 receptor comprising;
  (a) a first container comprising the polymorphic form of Compound 1; and
  (b) a second container comprising an additional agent useful in the treatment of diseases or conditions mediated by PGD2 or other agonists at the CRTH2 receptor, wherein the additional active agent is selected from the agents listed in claim 12.

14. The composition of claim 12 wherein the additional active agent is montelukast.

15. A process for the preparation of the pharmaceutical or veterinary composition of claim 10, comprising bringing into association the polymorphic form of Compound 1 and a pharmaceutically or veterinarily acceptable excipient.

16. A product comprising the polymorphic form of Compound 1 and one or more of the agents listed in claim 12 as a combined preparation for simultaneous, separate, or sequential use in the treatment of a disease or condition mediated by the action of $PGD_2$ at the CRTH2 receptor.

* * * * *